(12) United States Patent
Hanks et al.

(10) Patent No.: US 11,857,294 B2
(45) Date of Patent: Jan. 2, 2024

(54) MEDICAL DEVICES FOR MEASURING TISSUE PROPERTIES AND METHODS OF USE

(71) Applicant: Texas A&M University, College Station, TX (US)

(72) Inventors: John Hanks, Austin, TX (US); Amir Tofighi Zavareh, College Station, TX (US); Michel Saint-Cyr, Scottsdale, AZ (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 17/980,737

(22) Filed: Nov. 4, 2022

(65) Prior Publication Data

US 2023/0133795 A1 May 4, 2023

Related U.S. Application Data

(60) Provisional application No. 63/388,144, filed on Jul. 11, 2022, provisional application No. 63/275,489, filed on Nov. 4, 2021.

(51) Int. Cl.
*A61B 5/1455* (2006.01)
*A61B 5/0205* (2006.01)
(Continued)

(52) U.S. Cl.
CPC ........ *A61B 5/02055* (2013.01); *A61B 5/0022* (2013.01); *A61B 5/0261* (2013.01); *A61B 5/0537* (2013.01); *A61B 5/14551* (2013.01); *A61B 5/447* (2013.01); *A61B 5/4842* (2013.01); *A61B 5/6843* (2013.01); *A61B 5/7275* (2013.01); *G16H 10/60* (2018.01); *A61B 5/01* (2013.01); *A61B 5/721* (2013.01); *A61B 2090/0813* (2016.02); *A61B 2560/0223* (2013.01); *A61B 2560/0252* (2013.01);
(Continued)

(58) Field of Classification Search
CPC . A61B 5/0205; A61B 5/1455; A61B 5/14551; A61B 5/14552; A61B 5/14532; A61B 5/447; A61B 5/0261; A61B 5/0537; A61B 5/4842; A61B 5/7275; A61B 5/01; A61B 5/721

See application file for complete search history.

(56) References Cited

U.S. PATENT DOCUMENTS 5,638,818 A * 6/1997 Diab ................. A61B 5/02427
600/479
5,692,504 A * 12/1997 Essenpreis ............. G01N 21/47
600/316

(Continued)

*Primary Examiner* — Chu Chuan Liu
(74) *Attorney, Agent, or Firm* — Benjamin Aaron Adler

(57) ABSTRACT

Provided herein are medical devices, systems and platforms to monitor tissue properties such as oxygen saturation, temperature and degree of tissue edema for diagnosis and post-operative patient monitoring. The medical devices may be handheld or portable or may be removable patches. The medical devices utilize light of various visible and near-infrared wavelengths to interrogate a tissue where the intensities of reflected light correlate to one or more tissue property. Also provided are methods for measuring tissue properties, for detecting pressure ulcers and for remotely monitoring in real time a surgical flap on a post-operative subject via the medical devices.

11 Claims, 20 Drawing Sheets

(51) Int. Cl.
*A61B 5/0537* (2021.01)
*A61B 5/00* (2006.01)
*A61B 5/026* (2006.01)
*G16H 10/60* (2018.01)
*A61B 5/01* (2006.01)
*A61B 90/00* (2016.01)

(52) U.S. Cl.
CPC ............ *A61B 2562/0219* (2013.01); *A61B 2562/0247* (2013.01); *A61B 2562/166* (2013.01)

(56) References Cited

U.S. PATENT DOCUMENTS

| | | | | |
|---|---|---|---|---|
| 6,070,093 | A * | 5/2000 | Oosta | A61B 5/1455 |
| | | | | 600/316 |
| 8,064,989 | B2 * | 11/2011 | Brown | A61B 3/1225 |
| | | | | 600/407 |
| 2002/0161312 | A1 * | 10/2002 | Campbell | A61B 5/0531 |
| | | | | 600/547 |
| 2008/0130930 | A1 * | 6/2008 | Reithinger | A61B 5/6817 |
| | | | | 381/328 |
| 2013/0274565 | A1 * | 10/2013 | Langer | A61B 5/02455 |
| | | | | 600/595 |
| 2014/0288386 | A1 * | 9/2014 | Zand | A61B 5/14556 |
| | | | | 600/301 |
| 2017/0209081 | A1 * | 7/2017 | Davidson | A61B 5/1455 |

\* cited by examiner

MEDICAL DEVICES FOR MEASURING TISSUE PROPERTIES AND METHODS OF USE

CROSS-REFERENCE TO RELATED APPLICATIONS

This non-provisional application claims benefit of priority under 35 U.S.C. § 119(e) of provisional application U.S. Ser. No. 63/388,144, filed Jul. 11, 2022, and provisional application U.S. Ser. No. 63/275,489, filed Nov. 4, 2021, the entirety of both of which are hereby incorporated by reference.

BACKGROUND OF THE INVENTION

Field of the Invention

The present invention relates to the field of medical devices and diagnosis. More particularly, the present invention relates to handheld or portable wireless medical devices to measure tissue properties.

Description of the Related Art

More than 20% of people over the age of 60 years old have peripheral arterial disease (PAD) and 50% of these are undiagnosed. To diagnose PAD the traditional ankle brachial index, or ABI, with a Doppler test uses a blood pressure cuff to measure the systolic blood pressure in the lower legs and in the arms. The blood pressure cuff is inflated proximal to the artery in question until the Doppler device detects that the pulse in the artery ceases and then slowly deflated until the artery's pulse is re-detected. The pressure at that moment indicates the systolic pressure of that artery. The test is repeated on all four extremities. Well-established criteria for the ratio of the blood pressure in a leg compared to the blood pressure in the arms are used to assess the presence or absence of flow obstruction. Generally, these tests take 15 minutes to perform and require a vascular technician to be done properly.

Moreover, pressure ulcers, for example, bed sores, represent a significant health care cost globally. The standard of care today is visual inspection with tissue blanching which is a visual qualitative test performed by the clinician. In 2020, Bruin Biometrics received FDA clearance for a devices that uses capacitive measurement of the tissue. However, their device requires multiple measurements, i.e., comparative measurement of normal tissue and damaged tissue from the same patient. The sensitivity is 85% and specificity is 39%.

Furthermore, currently microsurgery and surgical flaps can accomplish functional and aesthetic reconstruction of tissues, and minimize donor site morbidity. However, about 5-7% of flap failures can still occur with vascular occlusion and surgical site infections being the two most common reasons for flap failures. Proper monitoring of surgical flaps for at least 2 weeks postoperation is crucial to avoid flap-related complications. Tissue oxygenation (StO2) and temperature are indicative of vascular occlusion and infections in the flap respectively, and any deviations from the normal conditions can indicate a possible flap failure. Currently, post-operative monitoring techniques involve wired devices that require the patients to stay in the hospital, which can present significant patient compliance issues and incur additional medical costs. Wired devices also can pose a hindrance to the surgical procedure.

There is a deficiency in medical devices to quickly measure and/or monitor various tissue properties in a patient and to transmit acquired data to a healthcare worker. Specifically, the prior art is deficient in handheld and portable medical devices that use multispectral wavelengths to measure tissue properties and wirelessly transmit the acquired data. The present invention fulfills this long-standing need and desire in the art.

SUMMARY OF THE INVENTION

The present invention is directed to a medical device for measuring tissue properties in a subject. A light-guiding cone comprises an opaque, anti-reflective, sloped surface and has optical properties that direct light along an optical excitation path into a homogeneous field on a tissue of interest in the subject. The light-guiding cone hosts a plurality of excitation light sources disposed at an open end thereof where each of the plurality emits light at a wavelength from visible to near infrared. An image sensor is configured to measure intensities of light with different wavelengths reflected from the tissue of interest. The light-guiding cone has a means for optically blocking light not reflected from the tissue of interest. A printed circuit board is in operable communication with the device and is configured to enable wireless communications and a processor and a memory tangibly store an algorithm that comprises processor-executable instructions for processing the reflected wavelengths as a measurement of tissue properties in electronic communication with the device.

The present invention is directed to a related medical device that further comprises a removable optically clear cap comprising a sterile barrier and disposed between the device and the tissue of interest, an optical diffuser positioned on the optical excitation path configured to direct the light into the homogeneous field on the tissue of interest, a temperature sensor to measure a surface temperature of the tissue of interest, at least one accelerometer to remove effects of tissue or device movement during data calibration or during data acquisition, or a display to monitor tissue properties or a combination thereof. The present invention also is directed to a related medical device in which the light-guiding cone further comprises an impedance sensor for detecting moisture content in the tissue.

The present invention also is directed to a method for measuring tissue properties in a subject. In the method a tissue of interest in the subject is illuminated with a non-isosbestic wavelength emitted from the plurality of excitation light sources comprising the medical device described herein and a reflected non-isosbestic wavelength is measured via the image sensor comprising the device. The tissue of interest is illuminated with an isosbestic wavelength and a reflected isosbestic wavelength is measured. A ratiometric image sensor measurement of the reflected non-isosbestic wavelength to the reflected isosbestic wavelength is determined via the algorithm comprising the medical device and is correlated with at least one tissue property of the tissue of interest. The method steps are repeated at least once with another non-isosbestic wavelength and the isosbestic wavelength.

The present invention also is directed to a related method further comprising measuring the tissue properties to determine a baseline, measuring the tissue properties as the subject exercises, measuring the tissue properties during a recovery period after exercise is completed, measuring a recovery time of the tissue properties, and correlating, via the algorithm, the recovery time with an ankle brachial index in the subject or to predict severity of peripheral arterial disease in the subject.

The present invention is directed further to a medical device for detecting pressure ulcers in a tissue. The medical device has a plurality of excitation light sources to produce an excitation signal and at least one optical sensor configured to detect a spectral response to the excitation signal from the tissue. At least one processor is in operable communication with the optical sensor(s) and have a wireless network connection.

The present invention is directed to another related medical device that further comprises a disposable optically clear material removably positionable between the device and the tissue. The present invention also is directed to another related medical device that further comprises, in operable communication with the at least one processor, at least one temperature sensor, at least one pressure inducer, or at least one pressure sensor or a combination thereof.

The present invention is directed further still to a system to detect a pressure ulcer in a tissue. The system comprises the medical device described herein and an optically clear material that is removably positionable between the device and the tissue. A smart device is in wireless communication with the processor.

The present invention is directed further still to a method for detecting a pressure ulcer in a tissue of interest in a subject. In the method the medical device described herein is placed on the tissue of interest and the excitation signal from at least two of the plurality of excitation light sources is delivered thereto. An intensity of the light reflected from the tissue of interest is detected as electrical signals with the optical sensor. The electrical signals are converted to a ratiometric measure of deoxyhemoglobin and water in the tissue of interest which correlates with the presence or absence of the pressure ulcer in the tissue of interest. The method steps are not repeated or are repeated one or more times to determine whether the pressure ulcer is healing or worsening.

The present invention is directed to a related method where the medical device further comprises a pressure sensor and the method further comprises the measuring pressure returned from the illuminated tissue of interest, measuring a time decay of the intensity of the light reflected from the tissue of interest, and quantitating capillary refill based on the time decay at the measured pressure. The present invention also is directed to another related method further comprising sending the ratiometric measure to the smart device or updating an electronic health record or a combination thereof.

The present invention is directed further still to a platform for remote monitoring of a subject post flap surgery. The platform has a flap patch that is removably positionable on a flap on the subject post flap surgery that is configured to obtain periodic measurements of oxygen saturation ($StO_2$) and temperature at the flap and a control patch that is removably positionable on healthy tissue on the subject proximate to the flap patch that is configured to obtain periodically measurements of temperature of the healthy tissue. A reusable receiver is in wireless electronic communication simultaneously with the flap patch and the control patch and configured to transmit the measurements received from the flap patch and the control patch to a cloud server. In a related platform the reusable receiver further comprises a display.

The present invention is directed further still to a method for remotely monitoring in real time a surgical flap on a post-operative subject. In the method the flap patch and the control patch comprising the platform described herein are positioned on the surgical flap and on surrounding healthy tissue. Oxygen saturation ($StO_2$) and flap temperature of the surgical flap are measured simultaneously in real time via the flap patch and temperature of the healthy tissue via the control patch. The measured values of oxygen saturation of the surgical flap and of temperatures of the surgical flap and healthy tissue are wirelessly transmitted to a cloud server via the receiver and are compared remotely over time to monitor tissue health of the surgical flap on the post-operative subject.

Other and further aspects, features, benefits, and advantages of the present invention will be apparent from the following description of the presently preferred embodiments of the invention given for the purpose of disclosure.

BRIEF DESCRIPTION OF THE FIGURES

The appended drawings have been included herein so that the above-recited features, advantages, and objects of the invention will become clear and can be understood in detail. These drawings form a part of the specification. It is to be noted, however, that the appended drawings illustrate preferred embodiments of the invention and should not be considered to limit the scope of the invention.

FIG. 11C shows the predicted $StO_2$ value compared to the ground $StO_2$ value captured by the predicated device

DETAILED DESCRIPTION OF THE INVENTION

Figure 1A:
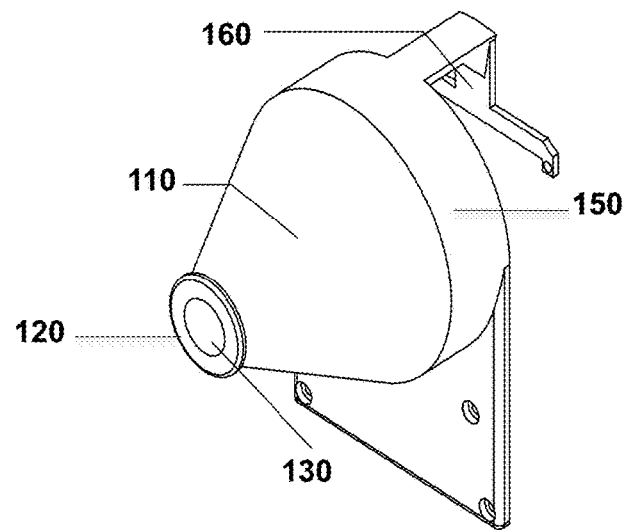
FIGS. 1A-1C are views of the front portion (FIGS. 1A-1B) and the back portion (FIG. 1C) of one embodiment of the medical device that measures tissue properties.

As used herein, the term "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method described herein can be implemented with respect to any other method described herein.

As used herein, the term "or" in the claims is used to mean "and/or" unless explicitly indicated to refer to alternatives only or the alternatives are mutually exclusive, although the disclosure supports a definition that refers to only alternatives and "and/or."

As used herein, "comprise" and its variations, such as "comprises" and "comprising," is understood to imply the inclusion of a stated item, element or step or group of items, elements or steps but not the exclusion of any other item, element or step or group of items, elements or steps unless the context requires otherwise. Similarly, "another" or "other" may mean at least a second or more of the same or different claim element or components thereof.

As used herein, the terms "subject" and "patient" are interchangeable and refer to any individual on which any of the medical devices described herein are used.

In one embodiment of the present invention there is provided a medical device for measuring tissue properties in a subject, comprising a light-guiding cone comprising an opaque, anti-reflective, sloped surface and having optical properties that direct light along an optical excitation path into a homogeneous field on a tissue of interest in the subject; a plurality of excitation light sources disposed at an open end of the light-guiding cone, each of the plurality emitting light at a wavelength from visible to near infrared; an image sensor configured to measure intensities of light with different wavelengths reflected from the tissue of interest; means for optically blocking light not reflected from the tissue of interest; a printed circuit board in operable communication with the device and configured to enable wireless communications; and a processor and a memory tangibly storing an algorithm comprising processor-executable instructions for processing the reflected wavelengths as a measurement of tissue properties in electronic communication with the device.

Further to this embodiment the device may comprise a removable optically clear cap comprising a sterile barrier and disposed between the device and the tissue of interest, an optical diffuser positioned on the optical excitation path configured to direct the light into the homogeneous field on the tissue of interest, a temperature sensor to measure a surface temperature of the tissue of interest, at least one accelerometer to remove effects of tissue or device movement during data calibration or during data acquisition, or a display to monitor tissue properties or a combination thereof. In another further embodiment the light-guiding cone may comprise an impedance sensor for detecting moisture content in the tissue. In yet another further embodiment the printed circuit board may comprise at least one accelerometer therewithin to quantify movements of the device.

In all embodiments the means for optically blocking light not reflected from the tissue of interest comprises a radially extruded lip at the end of the light-guiding cone disposed to cover an area of the tissue of interest under interrogation and to prevent ambient light from impinging on the area, the radially extruded lip comprising at least one pressure sensor configured to sense conformal attachment of the medical device to the surface of the tissue of interest. Also in all embodiments the light-guiding cone may comprise at least one reflective material and may be configured for automatic self-calibration. In addition one of the wavelengths emitted from the plurality of excitation light sources may be an isosbestic point of about 805 nm that enables a ratiometric image sensor measurement of a non-isosbestic wavelength to the isosbestic wavelength.

In all embodiments the algorithm may comprise processor-executable instructions configured to predict an Ankle Brachial Index (ABI) from measurements of tissue oxygenation, tissue temperature, or perfusion index or a combination thereof at at least one wavelength; correlate tissue oxygenation measurements from an upper limb and a lower limb of the subject to the Ankle Brachial Index (ABI); measure a photoplethysmography (PPG) signal; calculate distance from the image sensor to the tissue of interest via an analysis of patterns of light formed on the surface of the tissue of interest; predict the stage of at least one pressure ulcer in the subject as stage 1, stage 2, stage 3, or stage 4; predict sub-clinical stage 1 pressure ulcers in the subject; or predict peripheral artery disease in the subject; or a combination thereof.

In another embodiment of the present invention there is provided method for measuring tissue properties in a subject, comprising the steps of a) illuminating a tissue of interest in the subject with a non-isosbestic wavelength emitted from the plurality of excitation light sources comprising the medical device, as described supra; b) measuring a reflected non-isosbestic wavelength via the image sensor comprising the device; c) illuminating the tissue of interest with an isosbestic wavelength; d) measuring a reflected isosbestic wavelength; e) determining a ratiometric image sensor measurement of the reflected non-isosbestic wavelength to the reflected isosbestic wavelength via the algorithm comprising the medical device; f) correlating the ratiometric image sensor measurement with at least one tissue property of the tissue of interest; and g) repeating steps a) to f) at least once with another non-isosbestic wavelength and the isosbestic wavelength.

Further to this embodiment the method may comprise measuring the tissue properties to determine a baseline; measuring the tissue properties as the subject exercises; measuring the tissue properties during a recovery period after exercise is completed; measuring a recovery time of the tissue properties; and correlating, via the algorithm, the recovery time with an ankle brachial index in the subject or to predict severity of peripheral arterial disease in the subject. In both embodiments steps a) to d) may comprise illuminating sequentially the tissue of interest with a plurality of non-isosbestic wavelengths of differing wavelengths; measuring sequentially the plurality of reflected isosbestic wavelengths; illuminating sequentially the tissue of interest with a plurality of isosbestic wavelengths of differing wavelengths; and measuring sequentially the plurality of reflected isosbestic wavelengths.

In yet another embodiment of the present invention there is provided a medical device for detecting pressure ulcers in a tissue, comprising a plurality of excitation light sources to produce an excitation signal; at least one optical sensor configured to detect a spectral response to the excitation signal from the tissue; and at least one processor in operable communication with the optical sensor(s) and having a wireless network connection. Further to this embodiment the medical device may comprise a disposable optically clear material removably positionable between the device and the tissue. In another further embodiment the medical device may comprise, in operable communication with the at least one processor, at least one temperature sensor, at least one pressure inducer, or at least one pressure sensor or a combination thereof.

In all embodiments the plurality of excitation light sources may transmit at least two of a light with a 660 nm wavelength, a light with a 950 wavelength nm, or a light with a 800 nm wavelength. Also in all embodiments the processor may be configured to measure a spectral response of the tissue, to quantitate blood capillary refill rates, to determine a likelihood of the tissue developing a pressure ulcer, to communicate wirelessly with a smart device, or to update an electronic health record or a combination thereof.

In a related embodiment of the present invention there is provided a system to detect a pressure ulcer in a tissue, comprising the medical device described supra; an optically clear material removably positionable between the device and the tissue; and a smart device in wireless communication with the processor.

In yet another embodiment of the present invention there is provided a method for detecting a pressure ulcer in a tissue of interest in a subject, comprising the steps of a) placing the medical device described supra on the tissue of interest; b) delivering the excitation signal from at least two of the plurality of excitation light sources to the tissue of interest; c) detecting with the optical sensor an intensity of the light reflected from the tissue of interest as electrical signals; d) converting the electrical signals to a ratiometric measure of deoxyhemoglobin and water in the tissue of interest which correlates with the presence or absence of the pressure ulcer in the tissue of interest; and e) repeating steps a)-c) zero or more times to determine whether the pressure ulcer is healing or worsening.

Further to this embodiment the medical device may comprise a pressure sensor, the method comprising measuring pressure returned from the illuminated tissue of interest; measuring a time decay of the intensity of the light reflected from the tissue of interest; and quantitating capillary refill based on the time decay at the measured pressure. In another further embodiment the method comprises sending the ratiometric measure to the smart device or updating an electronic health record or a combination thereof. In all embodiments the plurality of excitation light sources may deliver excitation signals with a 660 nm wavelength to measure deoxyhemoglobin in the tissue of interest, transmit light with a 950 nm wavelength to measure water in the tissue of interest and transmit a reference light with a 800 nm wavelength that is an isosbestic point of deoxyhemoglobin and oxyhemoglobin.

In yet another embodiment of the present invention there is provided a platform for remote monitoring of a subject post flap surgery, comprising a flap patch removably positionable on a flap on the subject post flap surgery that is configured to obtain periodically measurements of oxygen saturation ($StO_2$) and temperature at the flap; a control patch removably positionable on healthy tissue on the subject proximate to the flap patch that is configured to obtain periodically measurements of temperature of the healthy tissue; and a reusable receiver in wireless electronic communication simultaneously with the flap patch and the control patch and configured to transmit the measurements received from the flap patch and the control patch to a cloud server. Further to this embodiment the reusable receiver may comprise a display.

In one aspect of all embodiments the flap patch may comprise an oxygen saturation ($StO_2$) patch with a plurality of LEDs that emit multispectral light and a photodiode that receives reflected light; a temperature patch with an ambient temperature sensor and a body temperature sensor; an insulator disposed around the temperature patch; and a controller in operable electronic communication with the oxygen saturation patch and the temperature patch. In this aspect the plurality of LEDs may emit multispectral light with wavelengths of 625 nm, 680 nm, 805 nm, and 870 nm. In another aspect of all embodiments the healthy tissue patch may comprise a temperature patch with an ambient temperature sensor and a body temperature sensor; an insulator disposed around the temperature patch; and a controller in operable electronic communication the temperature patch.

In yet another embodiment of the present invention there is provided a method for remotely monitoring in real time a surgical flap on a post-operative subject, comprising positioning the flap patch and the control patch comprising the platform described supra on the surgical flap and on surrounding healthy tissue; measuring simultaneously in real time oxygen saturation ($StO_2$) and flap temperature of the surgical flap via the flap patch and temperature of the healthy tissue via the control patch; wirelessly transmitting measured values of oxygen saturation of the surgical flap and of temperatures of the surgical flap and healthy tissue to a cloud server via the receiver; and comparing remotely the measured values over time to monitor tissue health of the surgical flap on the post-operative subject.

In one aspect of this embodiment the step of measuring the oxygen saturation may comprise delivering to the surgical flap light with a wavelength at an isosbestic point of blood oxygen, light at two non-isosbestic wavelengths below the isosbestic point and light at a non-isosbestic wavelength above the isosbestic point; measuring via the photodiode light reflected from the surgical flap; and calculating a ratiometric measurement of the non-isosbestic wavelengths to the isosbestic wavelength to determine the value in real time of the oxygen saturation in the surgical flap. In this aspect the isosbestic point may be 805 nm, the non-isosbestic wavelengths below the isosbestic point are 625 nm and 680 nm and the non-isosbestic wavelength above the isosbestic point is 870 nm.

Provided herein are medical devices, systems and methods for measuring tissue properties, for example, but not limited to oxygen saturation, the temperature of core and peripheral tissues, and/or tissue edema. Such measurements enable a healthcare provider to quickly diagnose such conditions as peripheral artery disease, pressure ulcers and the status of wounds and post-surgical flap tissue so that medical intervention may be initiated as is known and standard in the art.

The medical device may be handheld for ease of use on a patient, for example, in an office or clinic setting. The medical device may be portable, for example, of a size to fit in a pocket, where the healthcare provider can carry the device to the patient. The medical device may be embodied in a wireless enabled platform comprising patch that can be adhered to the patient for remote monitoring from the patient's home. The medical devices may comprise a display on which the results are read or may be enabled for wireless communication with an app on a smart device, such as, but not limited to, a smart phone or a tablet on which results are displayed. As such, the medical devices are in wireless communication with a cloud server, for example, a HIPAA compliant cloud server, from which a healthcare provider may download the results for review.

The handheld medical device has a cone with optical material properties, such as opacity and/or that is anti-reflective, to direct the light into a homogeneous field, an aperture at the small end of the cone that is directed at the tissue, means for optically blocking light non-reflected light, for example, an extruded lip radially disposed around the aperture at the small end, a consumable sterile cap that is optically transparent that is positioned on the surface of the tissue, a ring light of LEDs a the large end of the cone aperture with a plurality of wavelengths, one of the wavelengths is the isosbestic point (~805 nm) for oxygenated and deoxygenated blood, optical sensor with sensitivity from visible light to near infrared at the large aperture of the cone, an optical wall between the sensor and LED ring light to minimize light from the LED leaking into the sensor, optical diffuser in the optical path, X, Y, and Z accelerometers for detecting motion of the patient, a processor for algorithmic calculations, a look-up-table to predict ABI, a temperature sensor to measure the temperature at the surface of the tissue.

The light directing cone is placed on the ankle and wrist to measure optical tissue properties. The cone is designed to direct eight wavelengths of light from a ring of light emitting diodes (LEDs) emitted from an aperture at the small end of the cone to form a homogeneous field of light for each wavelength. Both visible and infrared light wavelengths emitted from the ring light on the tissue is scattered and reflected by the red blood cells coursing through the area of illumination. Returning light is detected by the sensor at the large end of the cone.

Tissue oxygenation or oxygen saturation in the medical field, is measured and calculated by using a change in the wavelengths intensity at the eight wavelengths and a software algorithm. Also, a blood flow (photoplethysmogram, PPG) waveform is instantaneously constructed. The changes in the wavelength intensity is a function of the oxygen in the blood. A software algorithm using the features of the eight wavelengths is used to calculate the $StO_2$. Unlike traditional $SpO_2$ readings a pulse waveform is not required to measure oxygen concentration. Both upper extremities (thenar eminence, wrist, and the forearm) and lower extremities (ankle, heel, arch, metatarsal, and toe) are interrogated, which takes about 10 seconds for each. A report form is generated that displays waveforms and the ratio of each leg measurement compared with the arms. Results are classified as Flow Obstruction or No Flow Obstruction. A regression to the Ankle Brachial Index, is performed and an ABI score is predicted.

The portable medical device is a low-cost device which measures the spectral response of ulcerated tissue using a minimum of two wavelengths, preferably three or more wavelengths, of light that are specific to pre-stage 1 pressure ulcers, wounds, and edema. A third wavelength is used as a reference signal. Light Emitting Diodes (LEDs) are used for the excitation signal and photodiodes or area sensors are used to sensing the returned light from the tissue. The device is configured to measure deoxyhemoglobin (approximately 660 nm or red light), water (approximately 950 nm or near infra-red light). The reference wavelength, is the isosbestic point for deoxyhemoglobin and oxyhemoglobin in blood, i.e., approximately 800 nm, 2nd near infra-red light. The ratio of electrical current measured at the photodiode for the deoxyhemoglobin signal to the isosbestic electrical current and the ratio of the electrical current measured at a photodiode for the water signal to the isosbestic current creates a ratiometric measurement that minimizes error and confounders, such as the amount of melanin in the dermal layer, and the distance of the LED excitation source and photodiode from the tissue.

The result is the equivalent of a sub-epidermal measurement of the amount of deoxyhemoglobin and water in the tissue. Pre-stage 1 and stage 1 pressure ulcers, edema, and wounds have a higher ratio of deoxyhemoglobin and water. An algorithm based on the results from clinical studies for normal tissue, pre-stage 1, and stage 1 pressure ulcers results in an early indication or alarm to alert the healthcare worker that an ulcer is forming. In addition, there is a unique optically clear device that opto-mechanically couples the device to the tissue.

The portable medical device is disposable and acts as a barrier between the instrumentation reader and the patient. A pressure sensor may be added to the system to simultaneously measure pressure as well as the light intensity returned from the tissue. The measure of the time decay of the return light signal given a known pressure is a quantitative measure of capillary refill which is the qualitative measure made by practitioners today.

The wireless platform comprises a BLUETOOTH-enabled flap patch, a control or healthy tissue patch and a reusable receiver which is a display device. Both the flap patch and control patch continuously send data via BLUETOOTH to the receiver. The components are compressed into a 30×30 mm sized flap patch and have the electronic circuitry to drive the light-emitting diodes and a photodiode that measures the reflected light. All the electronic circuitry is controlled via a computing center where the captured results are collected. The returning light is sensed by a photodiode in the flap patch. The data is sent to a HIPAA-compliant cloud server by a BLUETOOTH connection to the receiver/display device via a mobile app and data server architecture. Thus, the patients may be monitored remotely from their homes by the healthcare workers.

The LEDs in the flap patch are sources of the wavelength at the isosbestic point, 805 nm, two wavelengths, 625 nm and 680 nm, below the isosbestic point and one wavelength above the isosbestic point. The wavelengths below the isosbestic point have higher sensitivity and hence using two wavelengths below the isosbestic point increases measurement accuracy. The intensities of the reflected light are used to calculate oxygen saturation via a mobile app on the receiver/display as done for the handheld medical device. Particularly, healthy tissue temperature data from the control patch in addition to oxygen saturation and flap temperature data from the flap patch are sent via Bluetooth to the receiver which automatically uploads the data to the cloud.

Particular embodiments of the present invention are better illustrated with reference to the Figure(s), however, such reference is not meant to limit the present invention in any fashion. The embodiments and variations described in detail herein are to be interpreted by the appended claims and equivalents thereof.

Figure 1B:
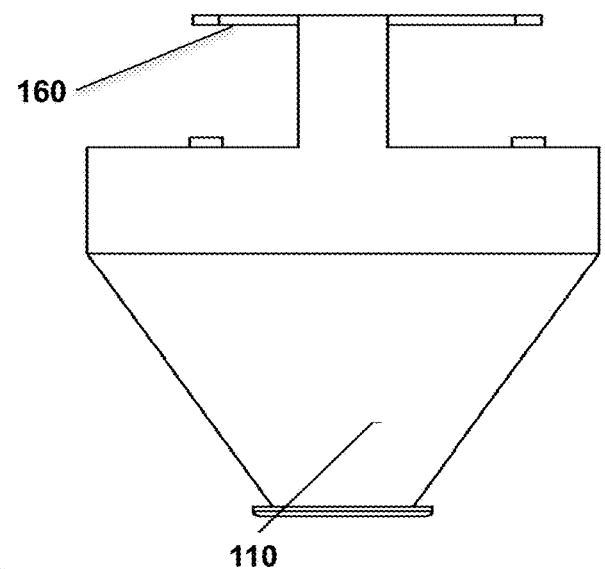
Figure 1C:
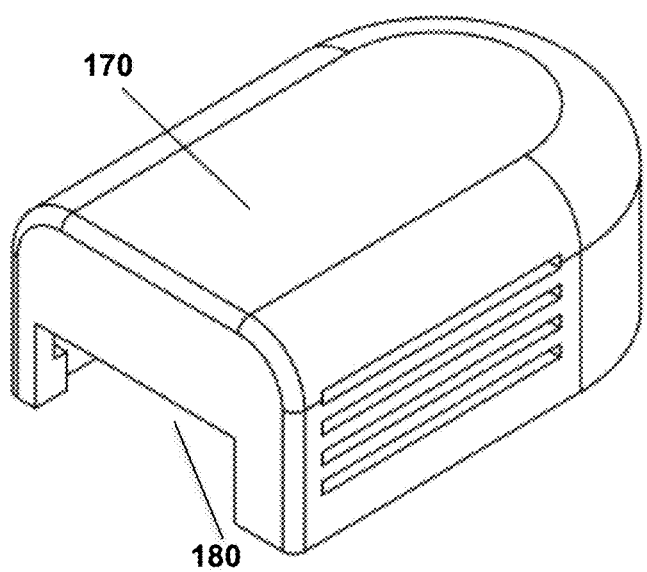

FIG. 1A is a perspective view of the exterior of the medical device showing the optical cone 110 having an extruded lip 120 around the open bottom end and an optically clear cap or tip covering 130 the bottom end. The bottom half of a casing 150 is formed at the top end of the optical cone. An accelerometer mount 160 extends from the bottom half of the casing. With continued reference to FIG. 1A, FIG. 1B is a top view of the optical cone 110 showing the accelerator mount 160. FIG. 1C is a perspective view of the top half of the casing 170 with an open interior cavity 180 configured to contain the accelerometer mount therein and to secure to the bottom half of the casing.

Figure 2:
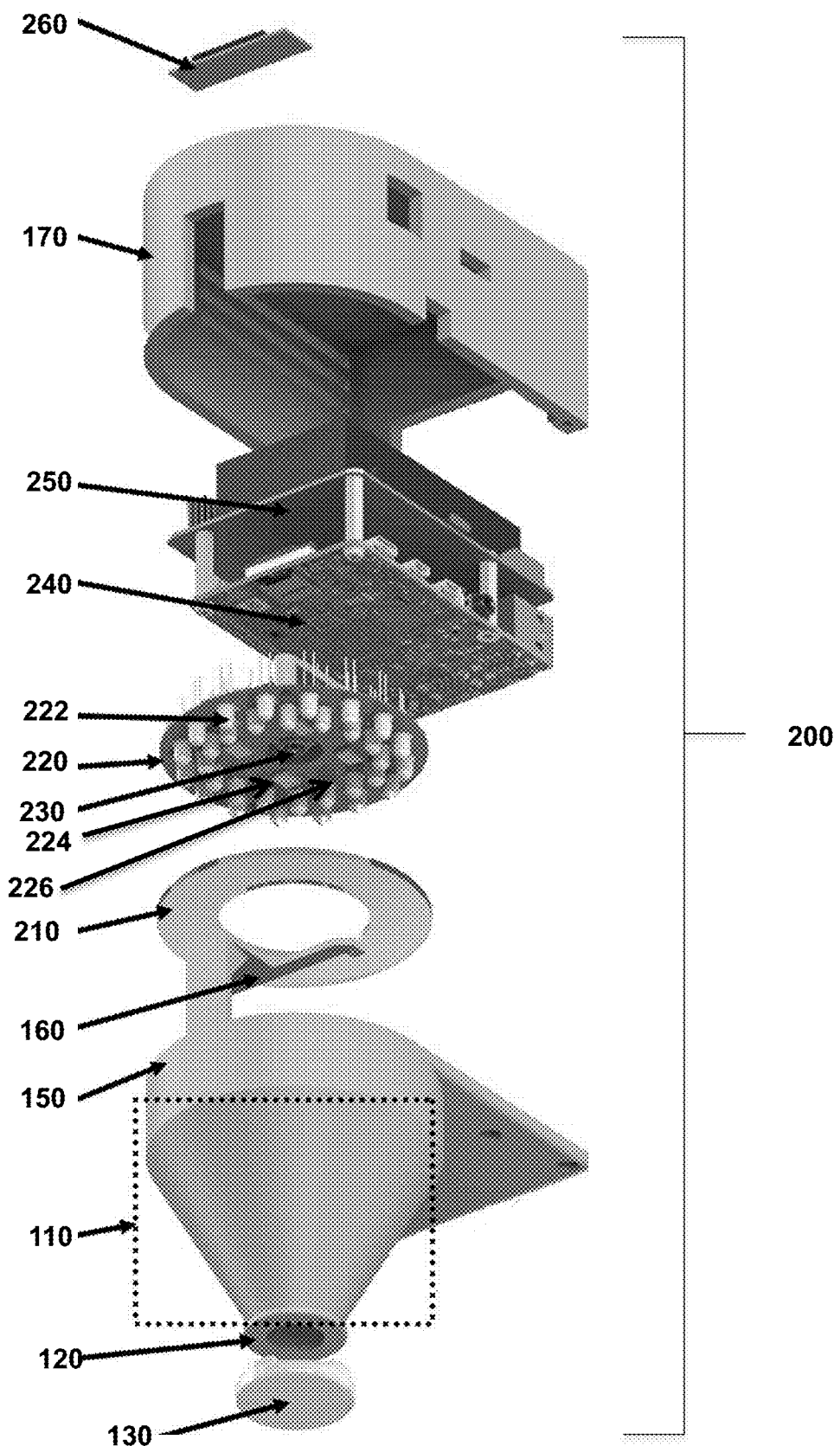
FIG. 2 is an exploded view of the medical device.

FIG. 2 is an exploded view of the medical device 200 showing the components in optical alignment. The clear tip 130 is disposed on the extruded lip 120 at the bottom end of the light guiding optical cone 110. The extruded lip blocks ambient light. An optical diffuser 210 is disposed behind the accelerometer mount 160 on the bottom half of the casing 150 and is in optical alignment with the clear tip. A printed circuit board (PCB) 220 has a plurality of LEDs represented by 222 as excitation light sources positioned on the PCB in line with the optical diffuser. The printed circuit board comprises LED drivers represented by 224 communicating on a 12C line and limiting resistors represented by 226 as are known in the art. The PCB has an aperture in the center aligned with the clear tip to accommodate an image sensor or camera sensor 230 to capture reflected light. The PCB and image sensor are in electronic communication with a processor board 240 that is in operable communication with a power supply board 250. A display 260 is disposed on the outer surface of the top half of the casing 170 and is in electronic communication with the processor board.

Figure 3:
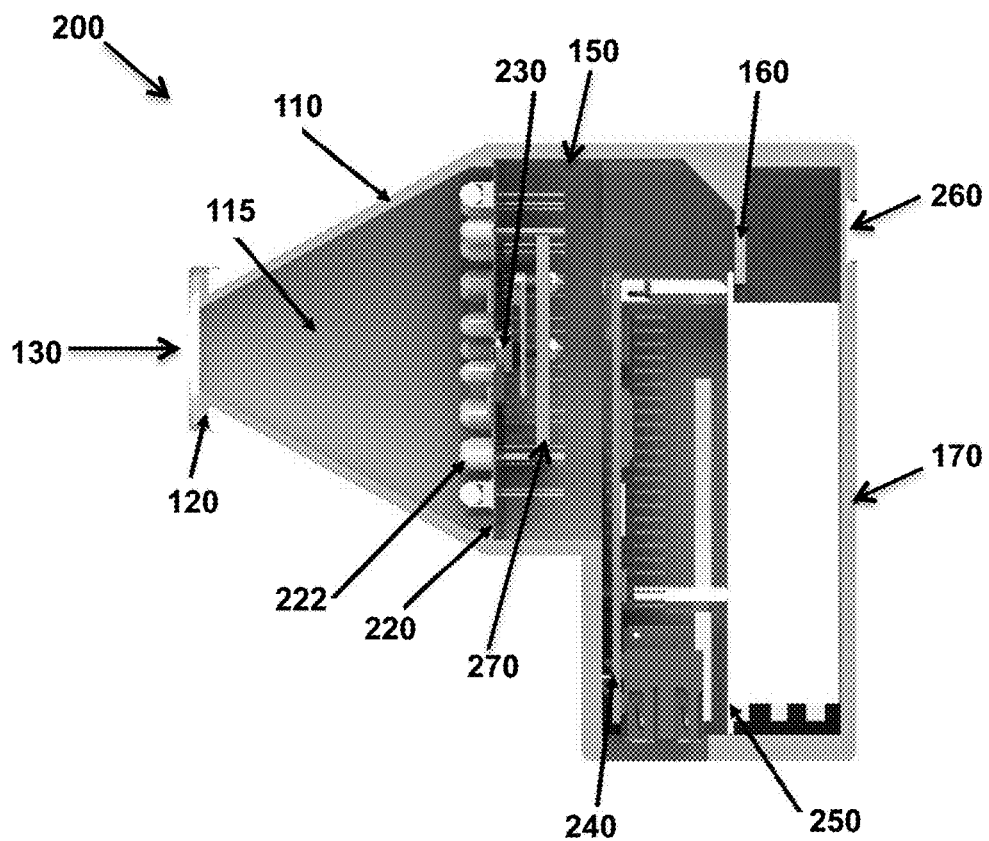
FIG. 3 is a cross-sectional view of the medical device of FIG. 2.

With continued reference to FIG. 2, FIG. 3 is a cross-sectional view of the handheld medical device 200. The clear tip 130 and extruded lips 120 are disposed exteriorly on the bottom end of the light guiding cone 110 which forms a light-guiding space 115. The printed circuit board 220 with the excitation light sources 222 and the image sensor 230 or camera sensor are secured to a camera mount 270 and disposed in the bottom half of the casing 150 formed on the light guiding cone. The processor board 240 and power supply board 250 are disposed within the top half of the casing 170 between the image sensor 230 and the accelerometer mount 160. The display 260 is on the outer surface of the casing 170 top half and the casing top half is secured to the casing bottom half to enclose the components.

Figure 4:
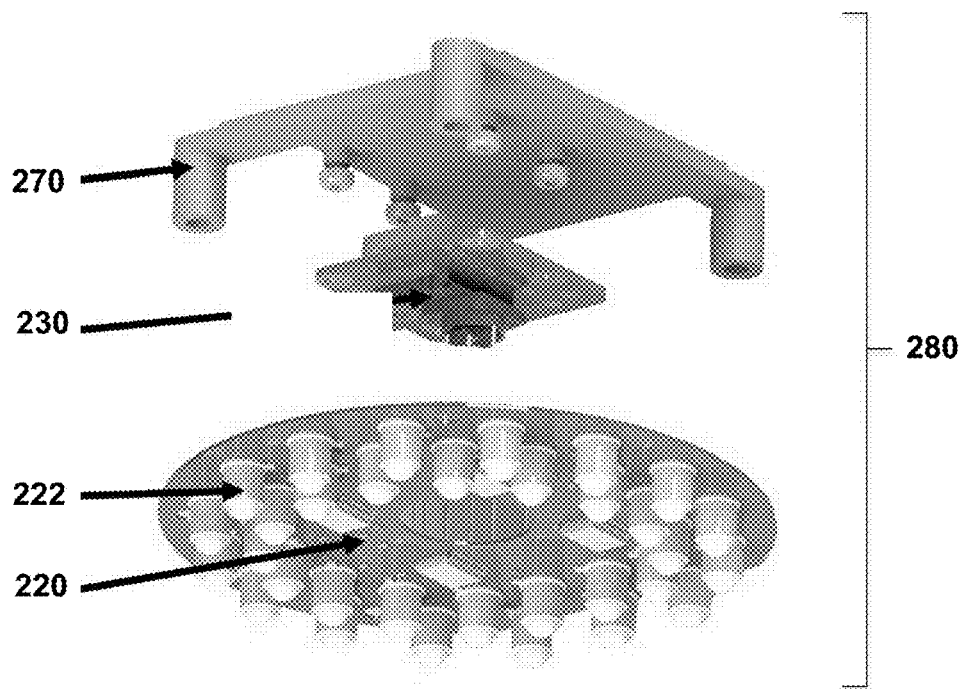
FIG. 4 is an exploded view of the arrangement of components comprising the camera in the medical device in FIG. 3.

With continued reference to FIGS. 2-3, FIG. 4 is an exploded view showing the alignment 280 of the printed circuit board 220 with LEDs 222 to the camera sensor 230 and attachment of both to the camera mount 270.

Figure 5A:
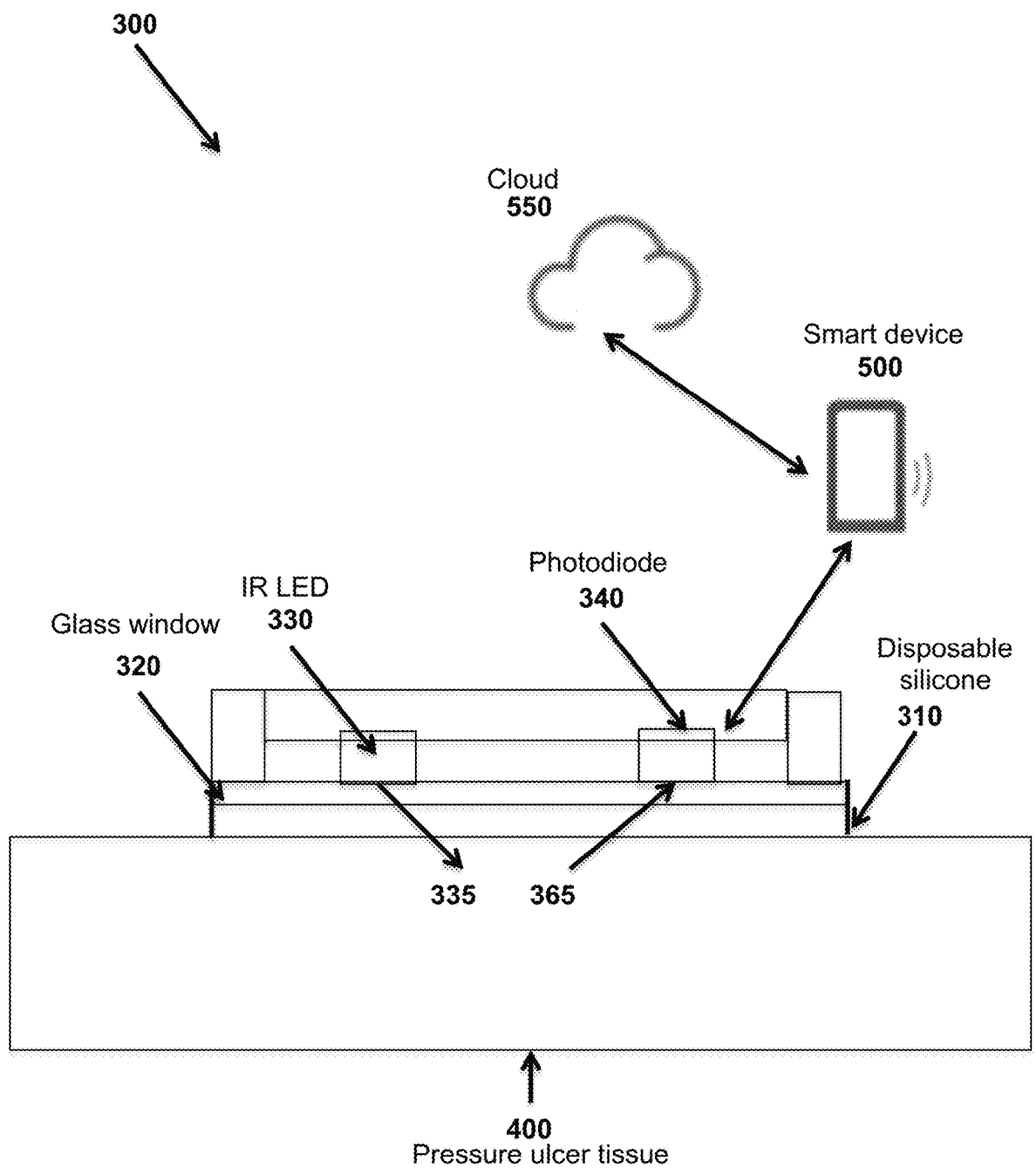
FIGS. 5A-5B are cross-sectional views of another embodiment of the medical device that detects pressure ulcers illustrating the device without (FIG. 5A) and with (FIG. 5B) a pressure sensor.
Figure 5B:
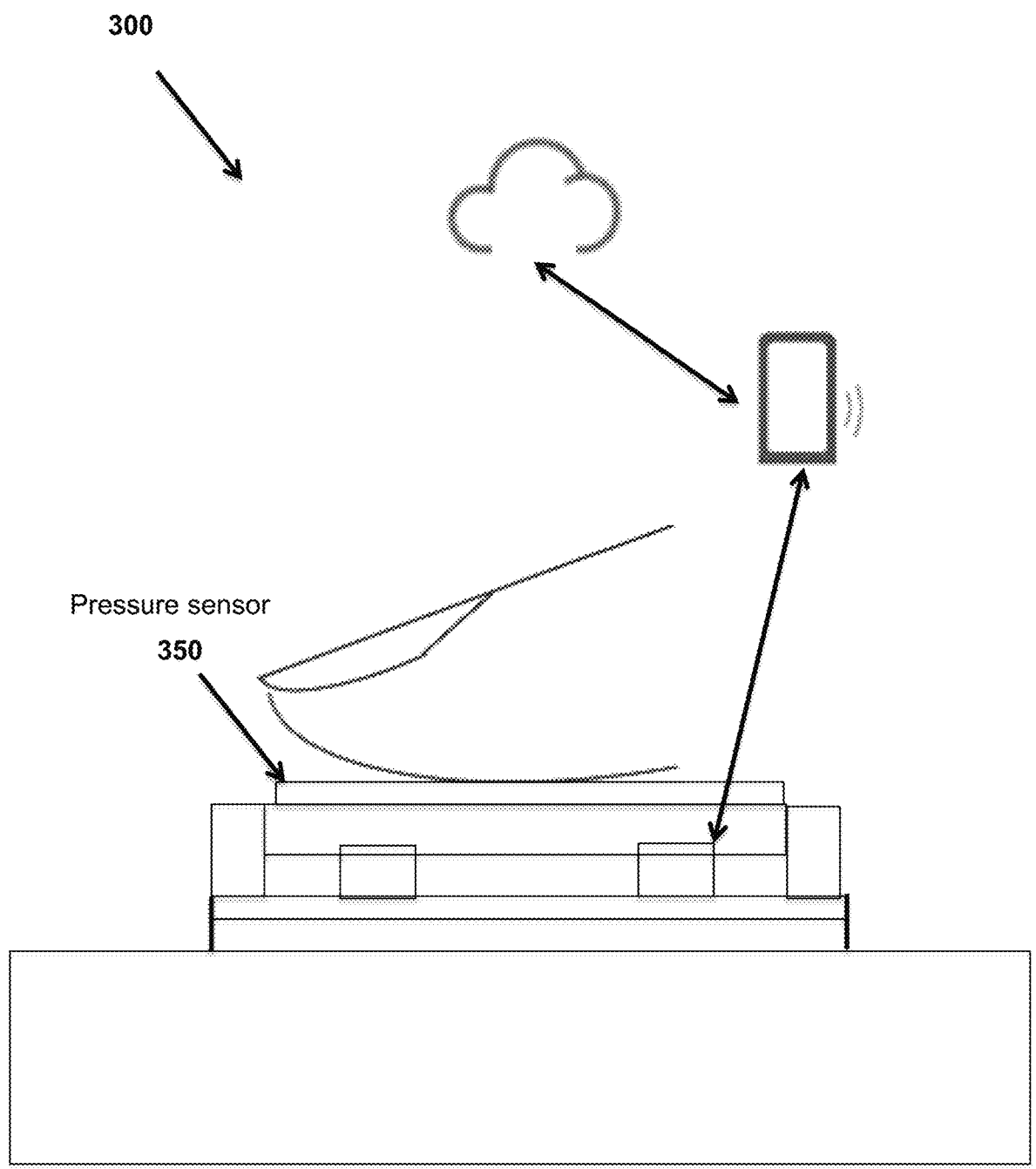

FIG. 5A illustrates the arrangement of the components of the portable medical device 300. A disposable silicon layer 310 is placed between the tissue 400 on the subject, for example, pressure ulcer tissue and the glass window 320 on the portable medical device. The infrared LED 330 and the photodiode 340 are in optical contact with the glass window such that light 335 from the infrared LED passes through the glass window and silicone layer to impinge on the pressure ulcer tissue. Reflected light 345 passes back through the silicon layer and glass window and is detected by the photodiode as raw data. The raw data is wirelessly transmitted to a smart device 500 which processes it to determine if and where edema is present in the tissue. The results may be displayed on the smart device and/or wirelessly transmitted to the cloud 550. With continued reference to FIG. 5A, FIG. 5B shows the placement of a pressure sensor 350 on the portable medical device 300.

Figure 6A:
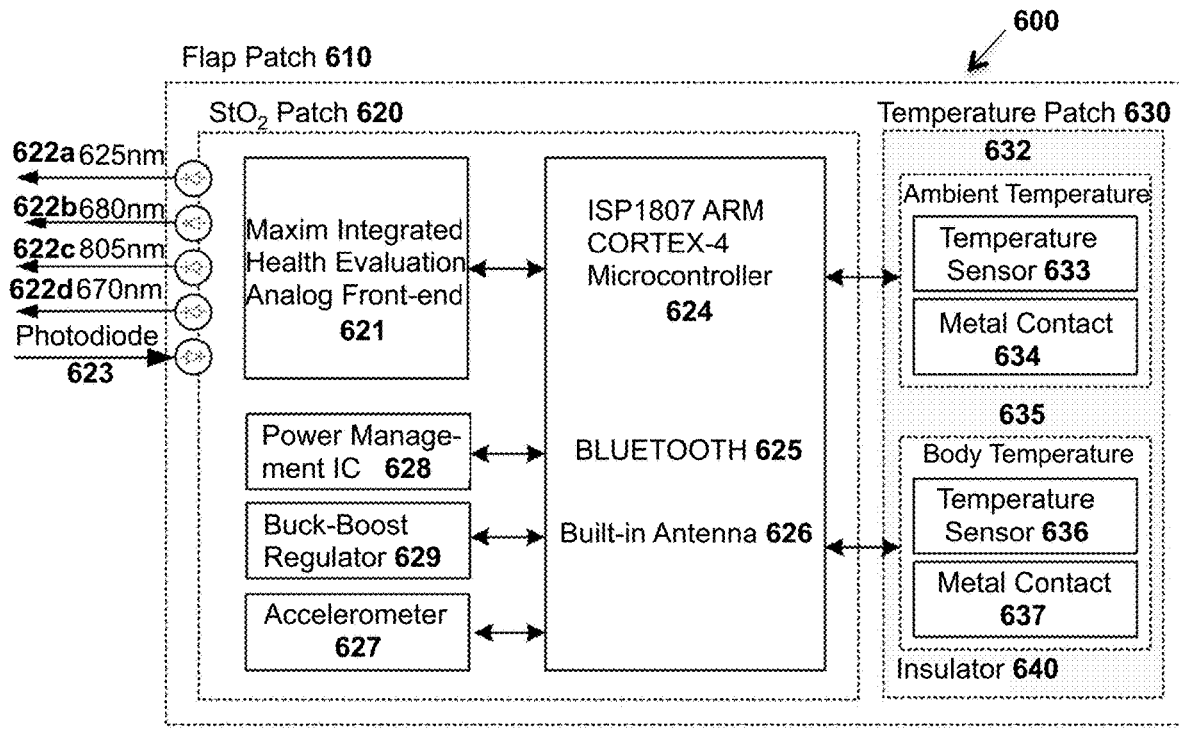
FIGS. 6A-6C are system diagrams of the flap patch (FIG. 6A) and the healthy tissue patch or control patch (FIG. 6B) of the platform configured to remotely monitor a patient after a flap surgery and of a cartoon illustrating the placement of the patches on a patient and their use (FIG. 6C).
Figure 6B:
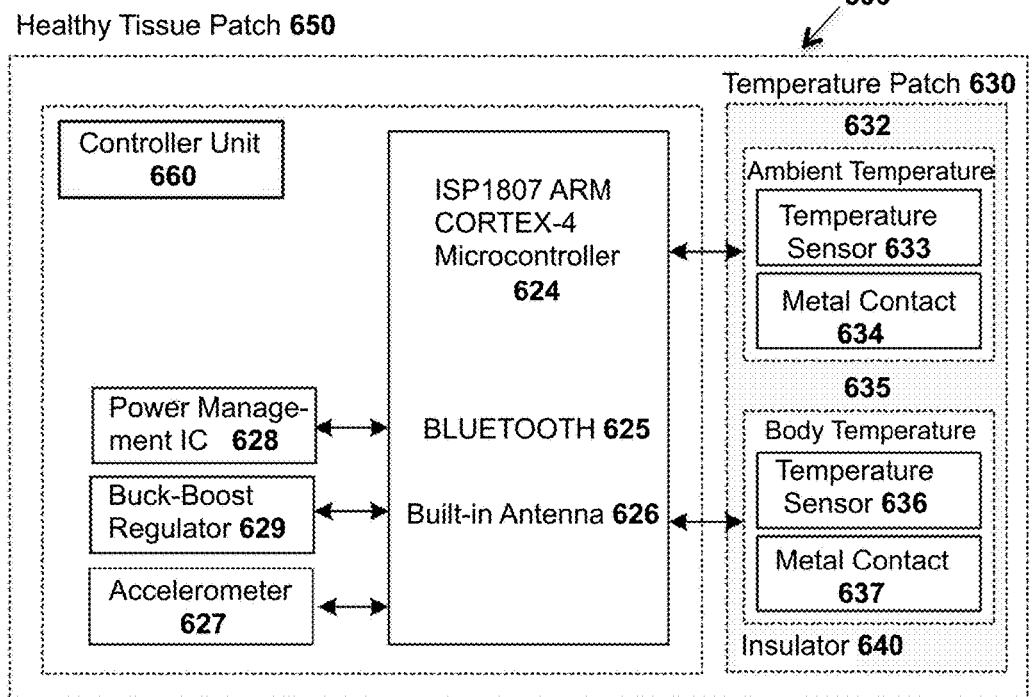

FIGS. 6A-6B are diagrams of the flap patch 610 and a healthy tissue patch 650 or control patch comprising a wireless platform 600 for remote monitoring of a flap on a post-surgical patient. The wireless platform also comprises a reusable receiver having a display (see FIG. 6C). FIG. 6A is the diagram of the flap patch which is removably adhered to the flap tissue (see FIG. 6C) to monitor oxygen saturation ($StO_2$) and body and ambient temperature. The flap patch utilizes a re-engineered MAXREFDES282 Health Patch Platform 6 621 to drive four LEDs 622*a,b,c,d* each emitting light with one of the wavelengths of 625 nm, 680 nm, 805 nm, and 870 nm and a photodiode 623 to capture light reflected from the flap tissue. The flap patch comprises an $StO_2$ patch 620 to measure oxygen saturation with the MAXREFDES282 patch as described and a temperature patch 630 for ambient temperature 632 and body temperature 635 monitoring with temperature sensors 633,636 and metal contacts 634,637 to better conduct heat from the surface of the tissue to the temperature sensor embedded within the device. An insulator 640 is disposed around the temperature patch to protect the sensors from the heat of the LEDs. The flap patch is BLUETOOTH 625 enabled and has a built-in antenna 626 to wirelessly transmit data to the reusable receiver. The flap patch comprises a microcontroller 624, for example an ISP1807 ARM CORTEX-4 microcontroller, in electronic and operable communication with the $StO_2$ patch and the temperature patch and with an accelerometer 627 and integrated circuitry configured for power management 628 of BLUETOOTH and circuitry to boost 629 the built-in antenna signal.

With continued reference to FIG. 6A, FIG. 6B is a diagram of the healthy tissue patch 630 or control patch. The healthy tissue patch differs from the flap patch 610 in that a controller unit 660 replaces the MAXREFDES282 platform 621, the LEDs 622*a,b,c,d* and the photodiode 623. The healthy tissue patch comprises, as does the flap patch, the temperature patch 630 with ambient temperature 632 and body temperature 635 sensors 633,636, metal contacts 634, 637 and insulator 640, and the microcontroller 624, BLUETOOTH 625, built-in antenna 626 and accelerometer 627 and associated circuitry 628,629 to wirelessly transmit temperature data to the reusable receiver (see FIG. 6C).

Figure 6C:
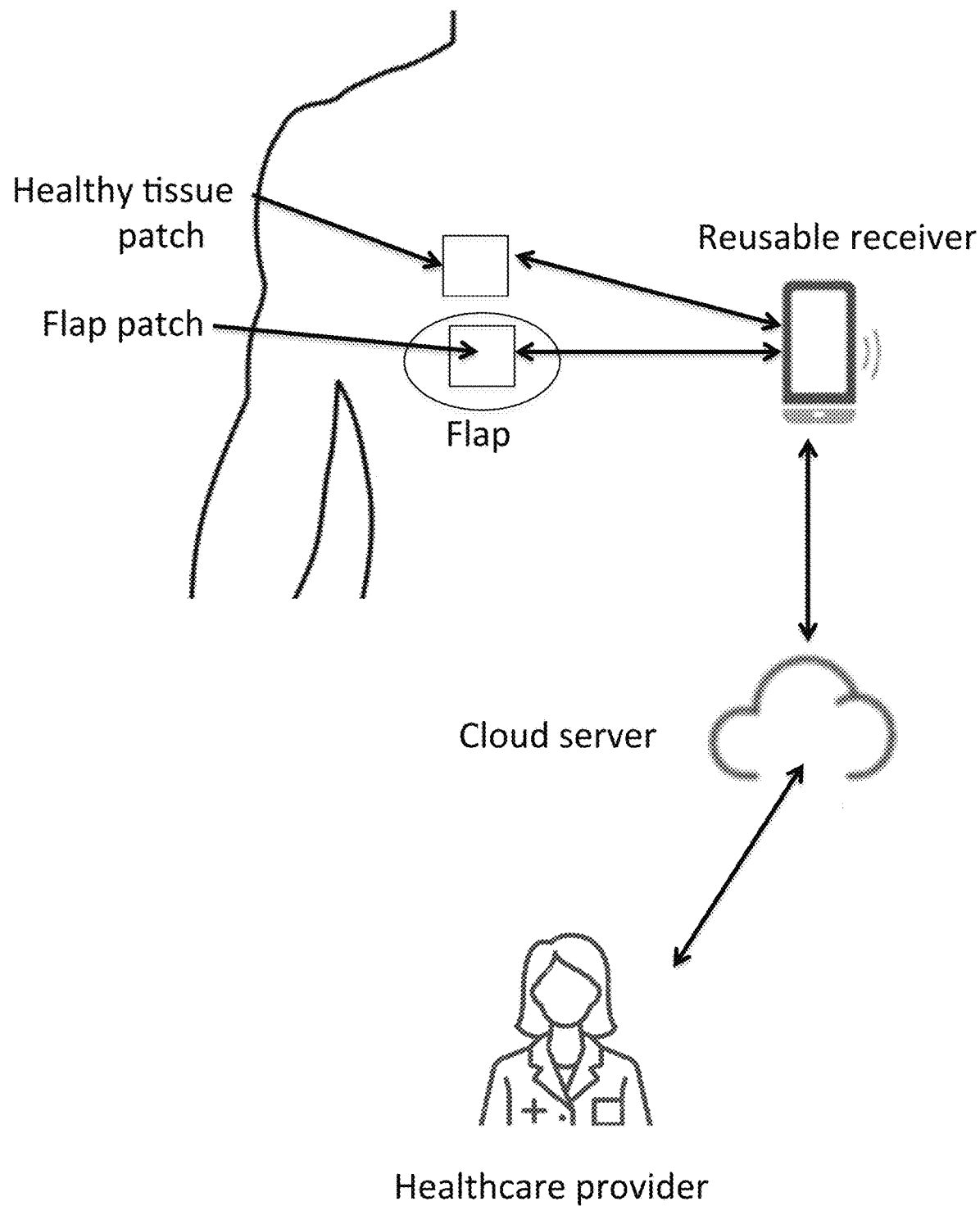

With continued reference to FIGS. 6A-6B, FIG. 6C is a cartoon illustrating the set-up of the wireless platform on a post-operative patient. The flap patch is placed on the surgical flap on the body of the post-operative patient and the healthy tissue patch is placed on healthy tissue. Both the flap patch and the healthy tissue patch wirelessly and continuously transmit raw data to the reusable receiver that automatically, wirelessly transmits the data to a cloud server. The healthcare provider is able to review the data to monitor the patient.

Figure 7:
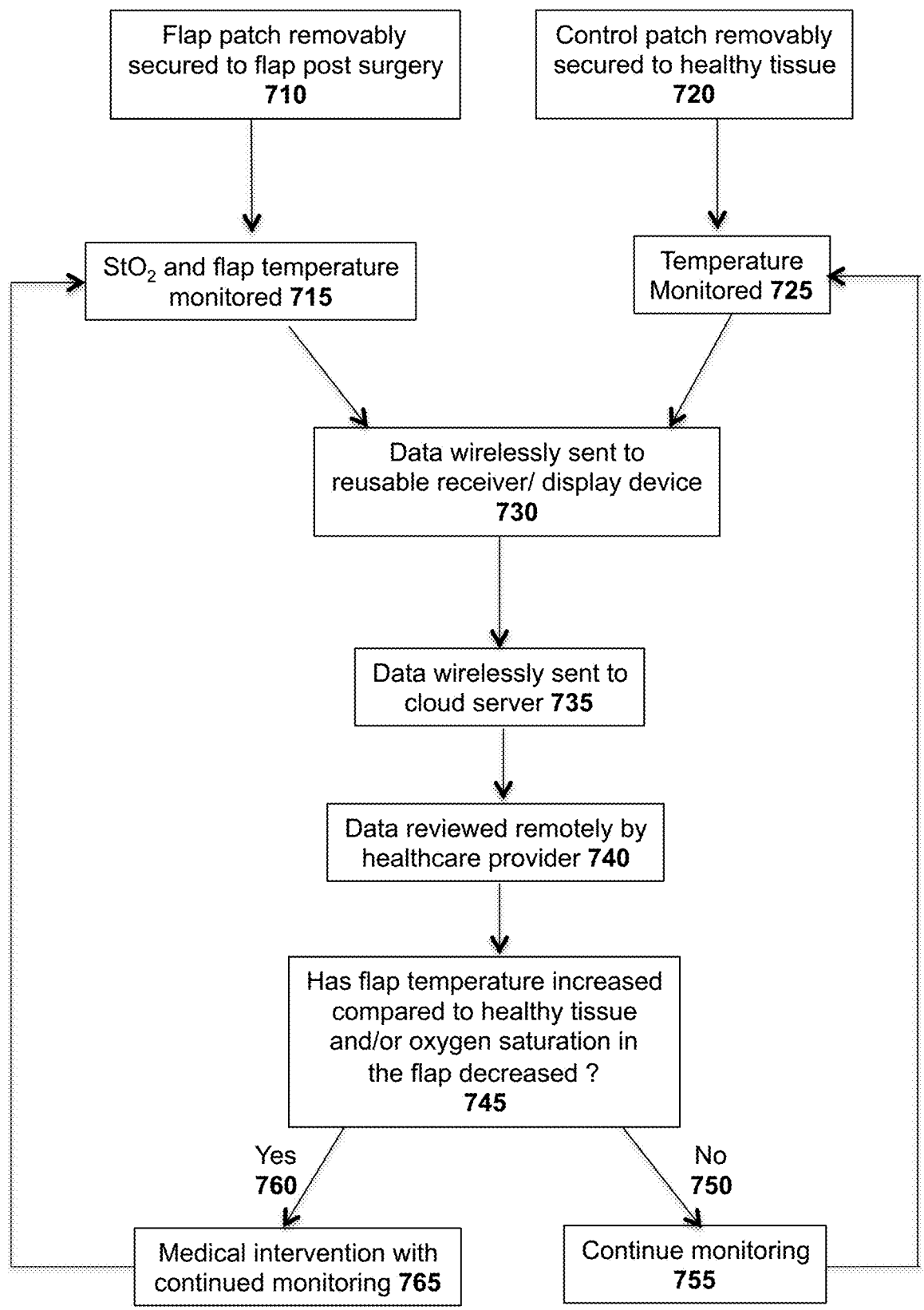
FIG. 7 is a flowchart illustrating how the platform functions.

FIG. 7 is a flowchart of the operation of the wireless platform. In a first step the flap patch and the control patch are removably secured to the post-surgical flap 710 and to healthy tissue 720 on the post-operative patient whereupon the oxygen saturation ($StO_2$) and temperature of the flap tissue and the temperature of the healthy tissue, as a control, are simultaneously and continuously monitored at 715, 725. In subsequent steps all the data is wirelessly sent to the reusable receiver with display at 730 which is automatically sent to a cloud server at 735, for example, a HIPAA compliant cloud server. A healthcare provider can review the data remotely at 740. The healthcare provider determines at 745 whether of not the flap temperature has increased compared to healthy tissue temperature and/or whether or not oxygen saturation of the flap tissue has decreased over time. If the answer is no at step 750 monitoring of the post-surgical flap continues at step 755. If flap temperature has increased and/or oxygen saturation decreased in the flap tissue, medical intervention with continued monitoring is provided at step 765. The healthcare provider determines the length of time it is necessary to monitor the patient.

The following examples are given for the purpose of illustrating various embodiments of the invention and are not meant to limit the present invention in any fashion.

Example 1

Figure 8A:
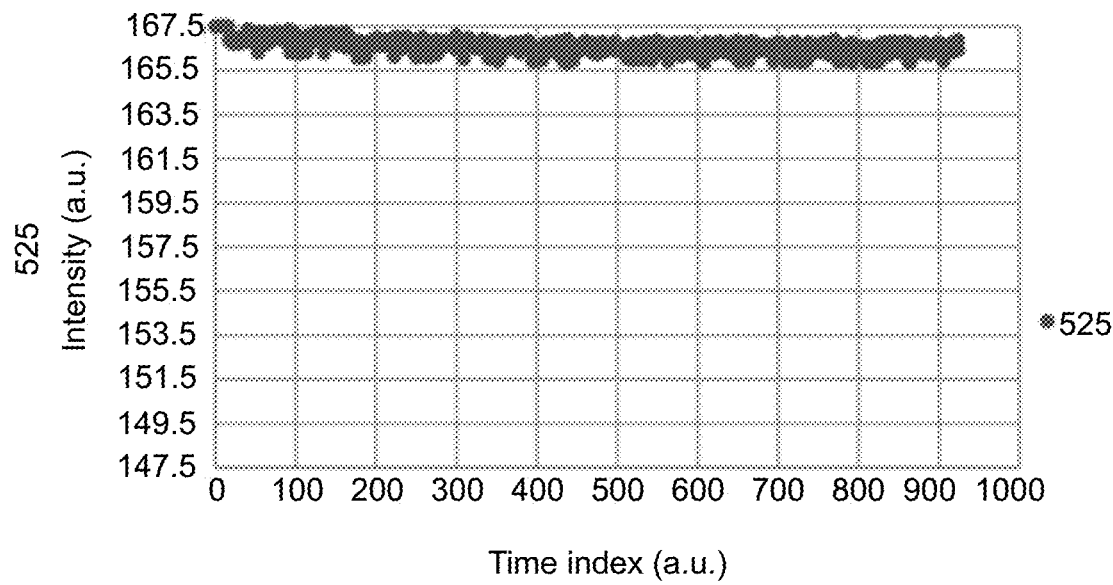
FIGS. 8A-8I show the results of reference white reflectance from interrogation at 525 nm (FIG. 8A) and the results when the thenar of a subject is illuminated with wavelengths of 525 nm (FIG. 8B), 590 nm (FIG. 8C), 625 nm (FIG. 8D), 690 nm (FIG. 8E), 780 nm (FIG. 8F), 810 nm (FIG. 8G), 870 nm (FIG. 8H), and 930 nm (FIG. 8I).
Figure 8B:
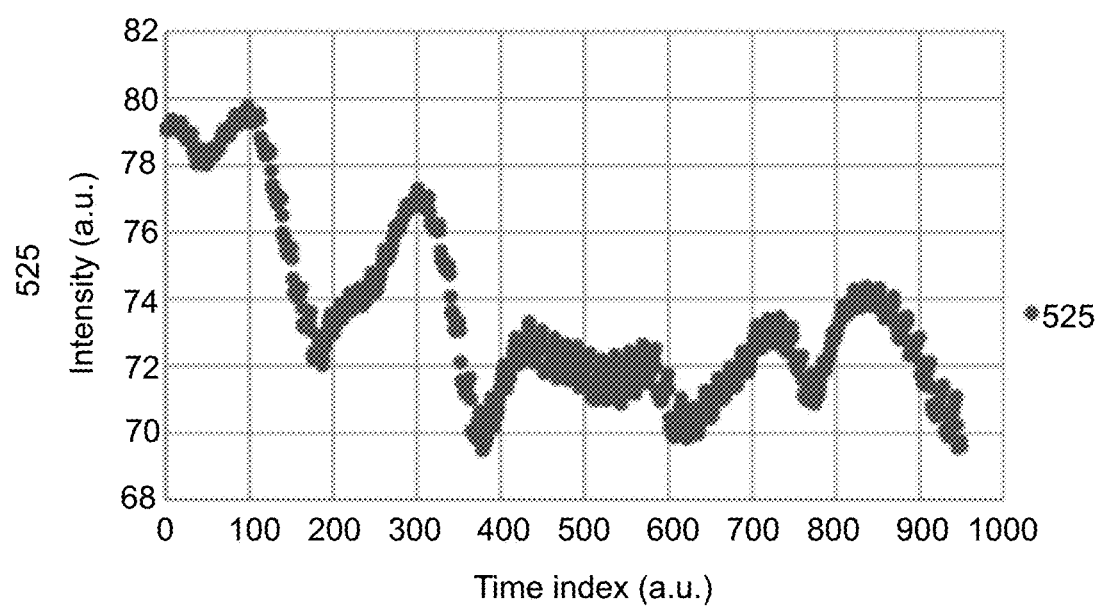
Figure 8C:
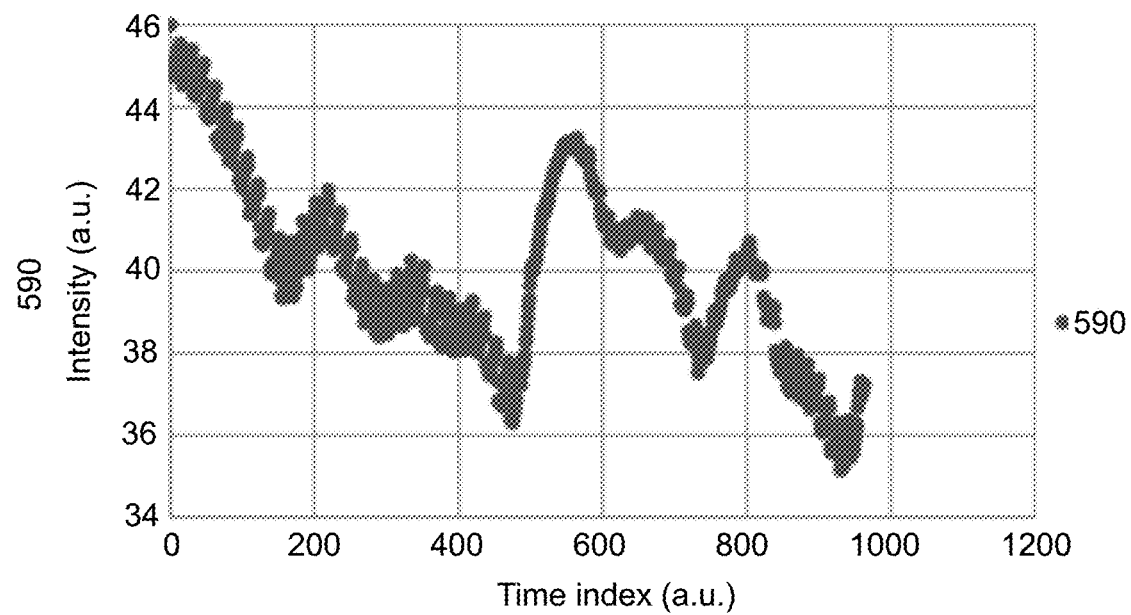
Figure 8D:
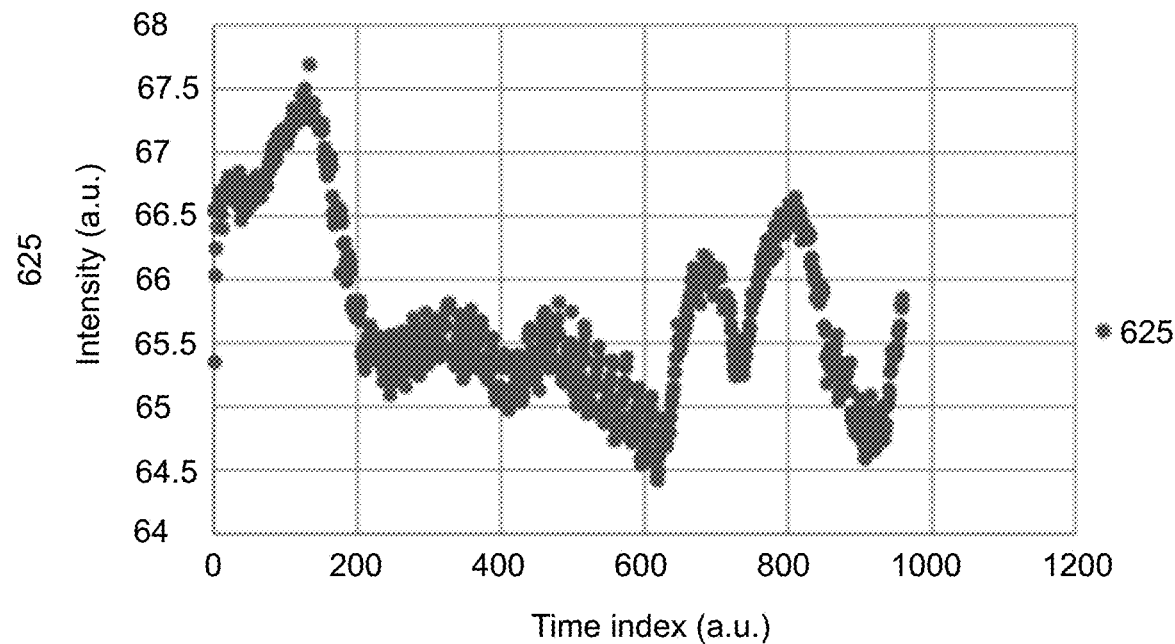
Figure 8E:
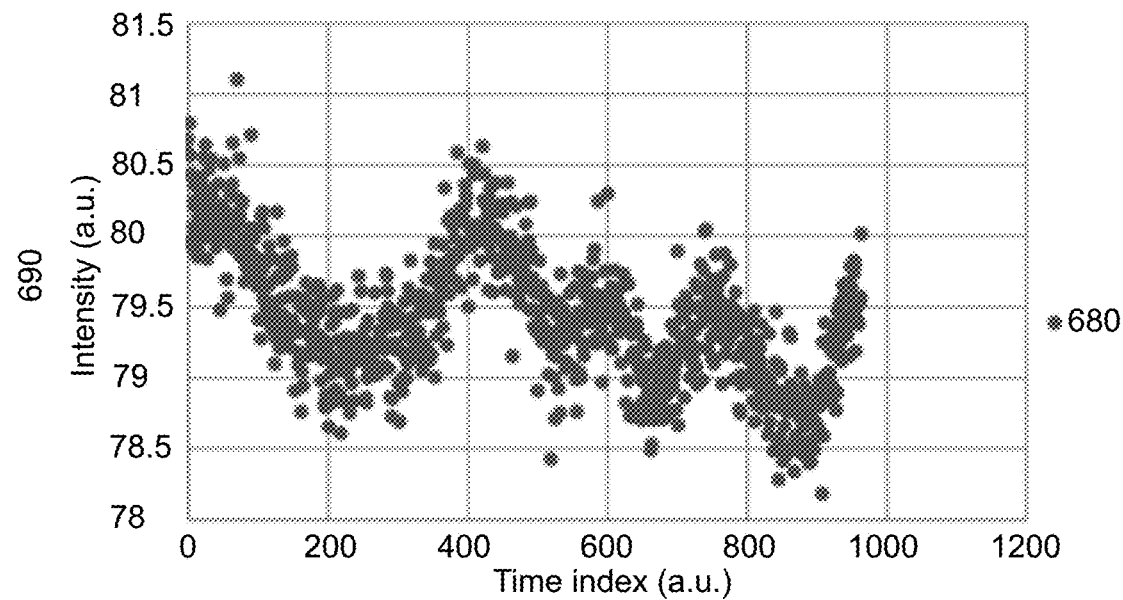
Figure 8F:
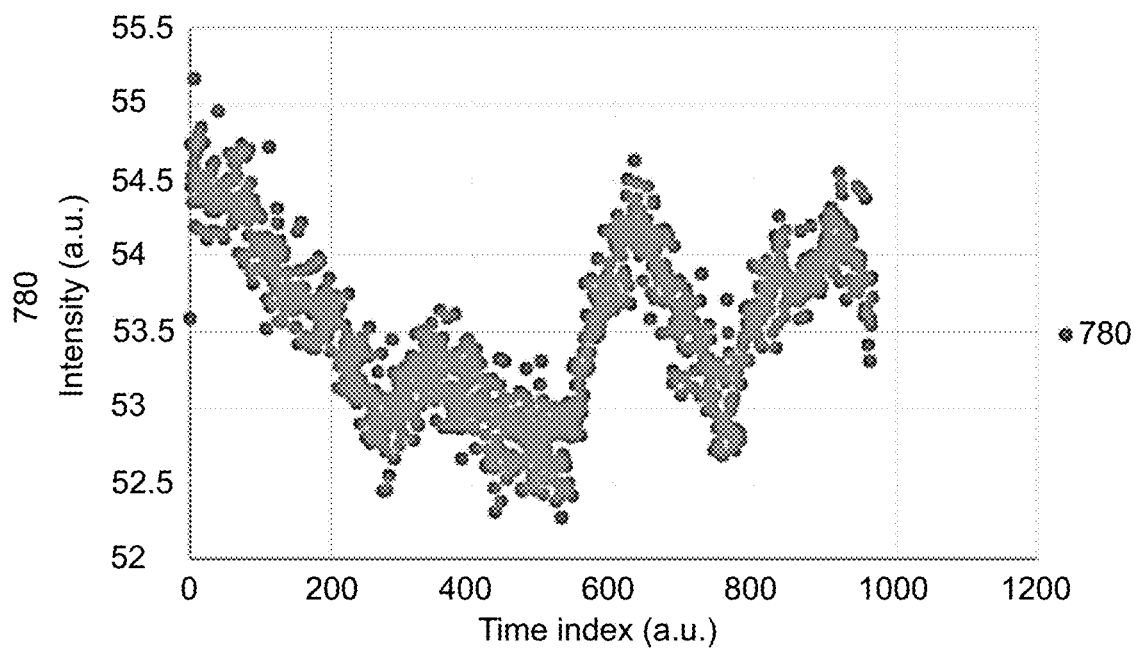
Figure 8G:
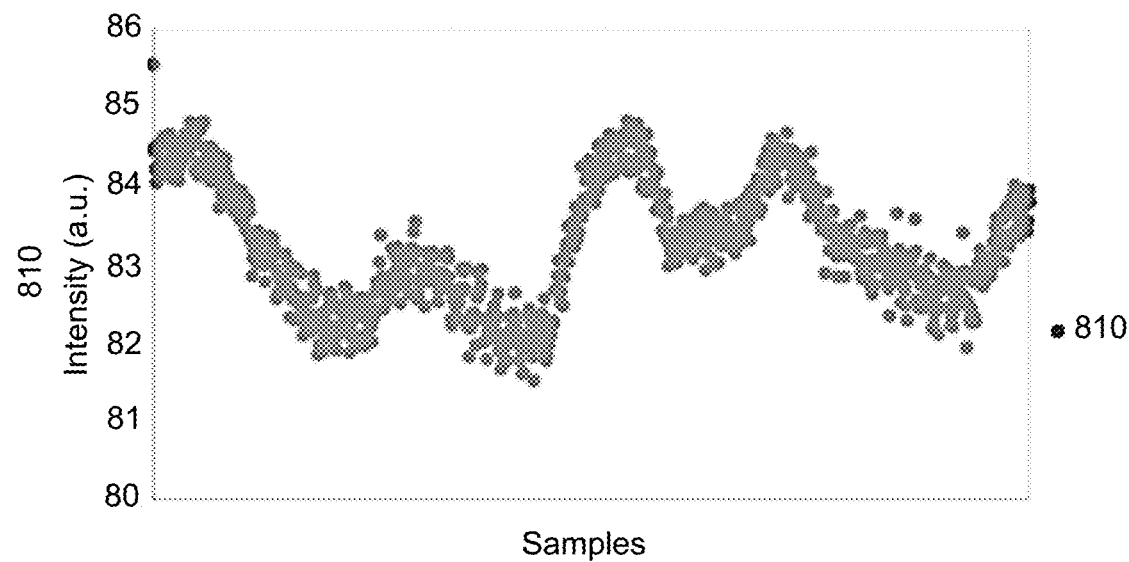
Figure 8H:
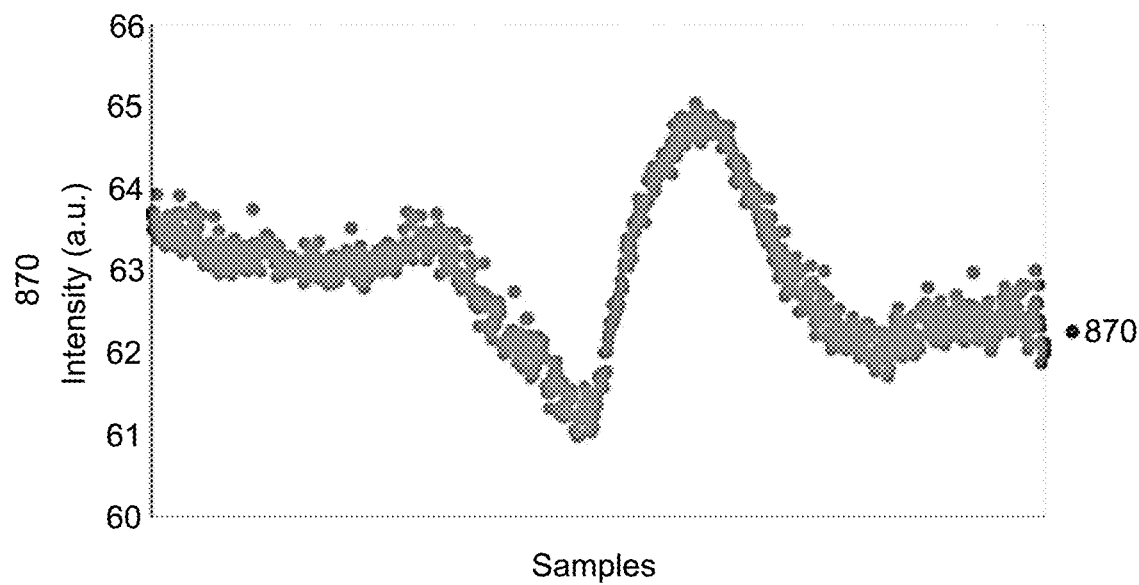
Figure 8I:
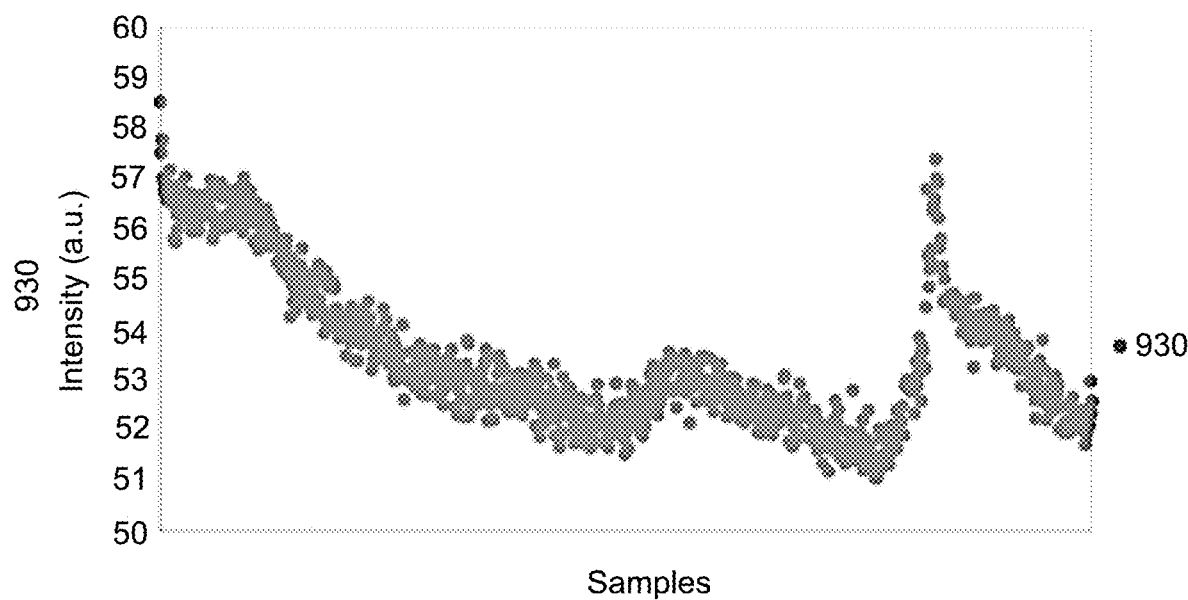

Medical Device: Handheld Device for Measuring Tissue Properties Reflectance: Comparison of Reflected Wavelength Intensities to Reference White Reflectance A reference white material is interrogated at 525 nm and the intensities of the reflected wavelengths measured (FIG. 8A). The standard deviation over mean error is calculated at 0.17%. The clear tip of the medical device (FIG. 2) is placed across the thenar area of a test subject's palm, excitation light with wavelengths of 525 nm, 590 nm, 625 nm, 690 nm, 780 nm, 810 nm, 870 nm, and 930 from the multispectral LEDs is delivered through the clear tip on the light guiding cone to the thenar whereupon light is reflected back through the clear tip and detected by the camera sensor in the image sensor and processed as reflected light intensity or reflectance. At 525 nm, 590 nm and 690 nm photoplethysmogram (PPG) data is observed (FIGS. 8B-8D). At all wavelengths (FIGS. 8B-8I) the blood circulation to the hand remains untouched. Standard deviations over mean error of 3.66%, 5.60%, 1.08%, 0.58%, 1.01%, 0.93%, and 1.31% (FIGS. 8B-8I) was observed when a reference white material is interrogated. Table 1 shows the mean, standard deviation and error at each wavelength.

TABLE 1

| Excitation wavelength (nm) | Mean | Standard Deviation | Error |
|---|---|---|---|
| Reference White Reflectance | | | |
| 525 Thenar | 166.5795033 | 0.2756406461 | 0.001654709256 |
| 525 | 73.51602601 | 2.692706624 | 0.03662747798 |
| 590 | 39.9464242 | 2.239496496 | 0.056062502 |
| 625 | 65.72921322 | 0.710308578 | 0.010806589 |
| 690 | 79.4244128 | 0.4670522 | 0.00588046 |
| 780 | 53.5456747 | 0.54229869 | 0.01012778 |
| 810 | 83.230678 | 0.77458502 | 0.00930648 |
| 870 | 62.9219917 | 0.92628568 | 0.01313191 |
| 930 | 53.45018267 | 1.477670207 | 0.027645747 |

Cuff Test

Figure 9:
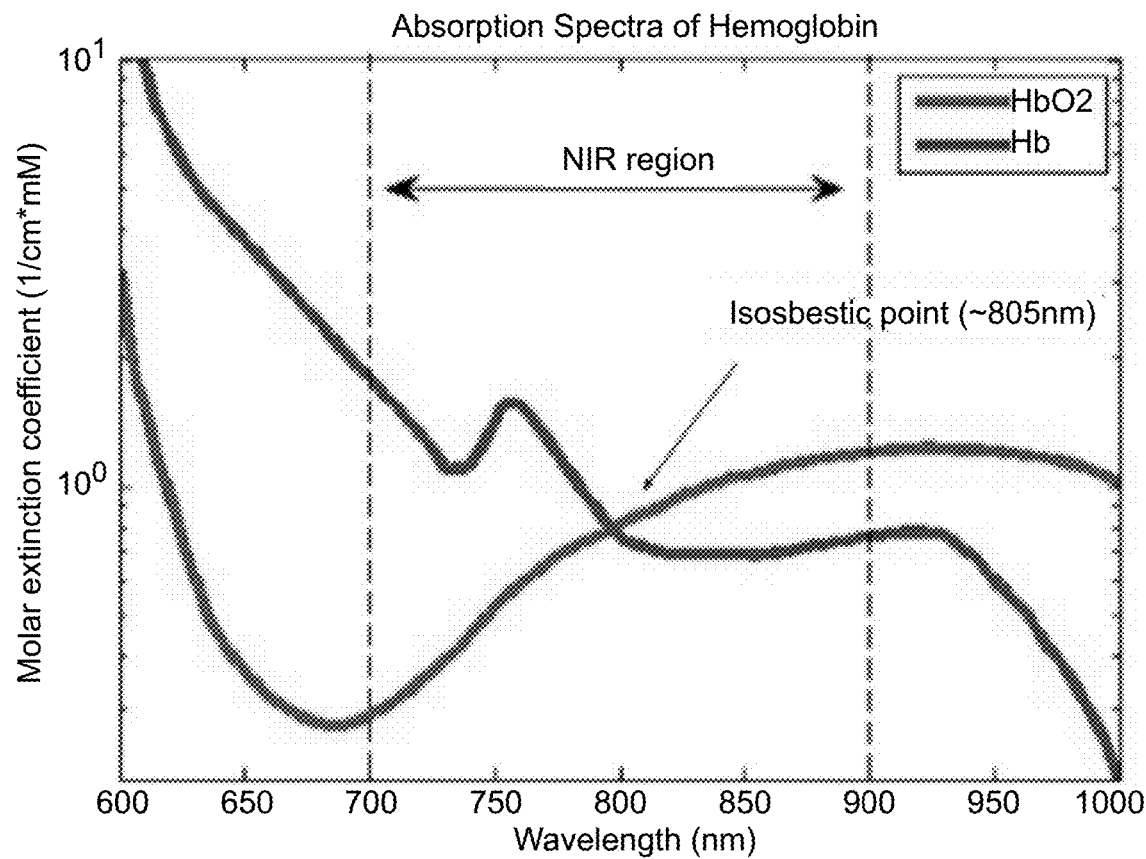
FIG. 9 is an absorption spectra of oxygenated hemoglobin (HbO2) and deoxygenated hemoglobin measuring the molar extinction coefficient from 600 nm to 1000 nm.

The blood circulation to the subject's arm was occluded by placing a blood pressure cuff on a patient's arm and pressurizing it at above the patient's systolic pressure and normalized intensities (intensity of reflected light at a certain wavelength over the intensity of the reflected light at 810 nm). Excitation light was delivered and reflected light intensities measured as described for the reflectance test. As time progresses, it is expected that the arm consumes the oxygen attached to hemoglobin cells and converts it to the deoxygenated form. Deoxygenated hemoglobin has higher absorption rate at wavelengths below 810 nm and a lower absorption rate at wavelengths above 810 nm. While the blood circulation is occluded, it is expected that the ratio of intensity of light at any wavelength below 810 nm over the intensity of light of 810 nm keeps declining and that the ratio of intensity of light at any wavelength above 810 nm over the intensity of light of 810 nm keep ascending (FIG. 9).

Figure 10A:
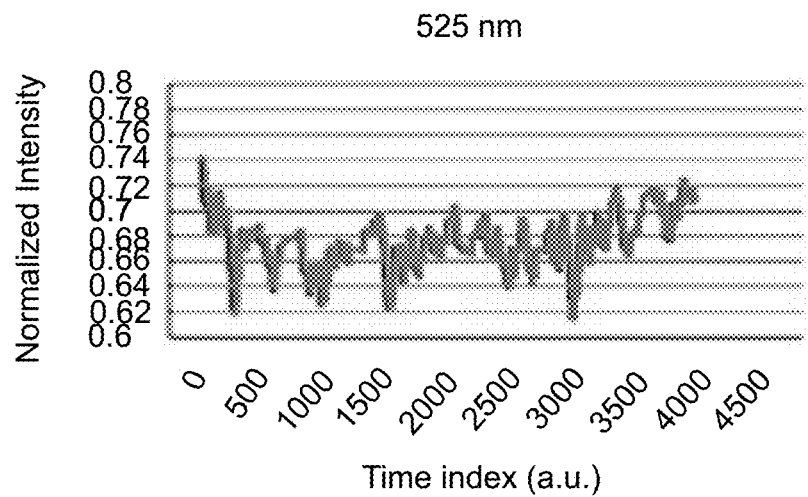
FIGS. 10A-10H show the results of the cuff test at 525 nm (FIG. 10A), 590 nm (FIG. 10B), 625 nm (FIG. 10C), 680 nm (FIG. 10D), 780 nm (FIG. 10E), (FIG. 10F), 870 nm (FIG. 10G), and 930 nm (FIG. 10H).
Figure 10B:
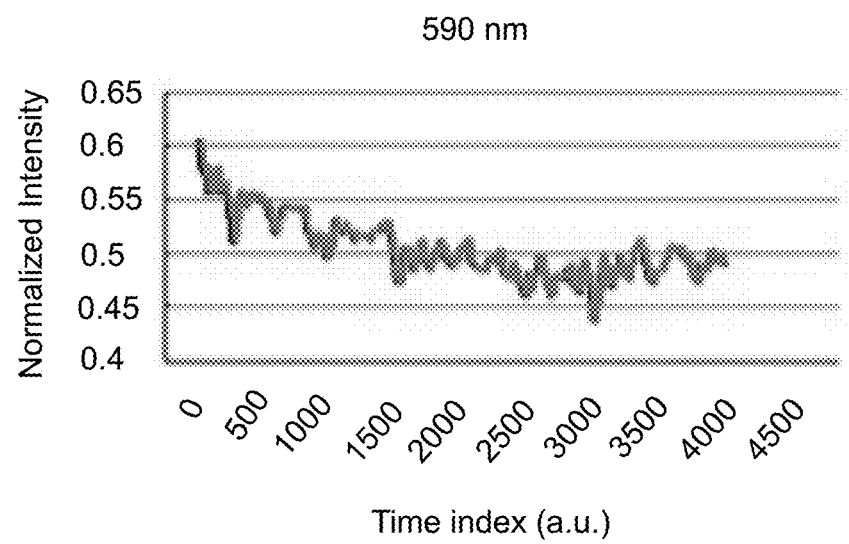
Figure 10C:
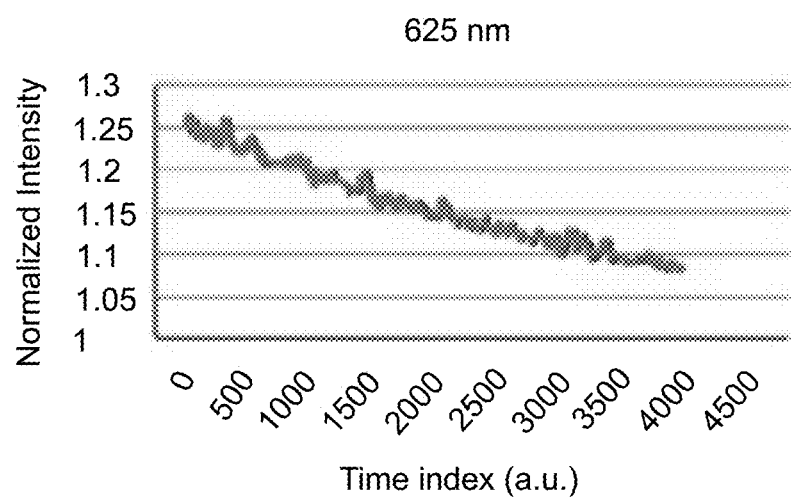
Figure 10D:
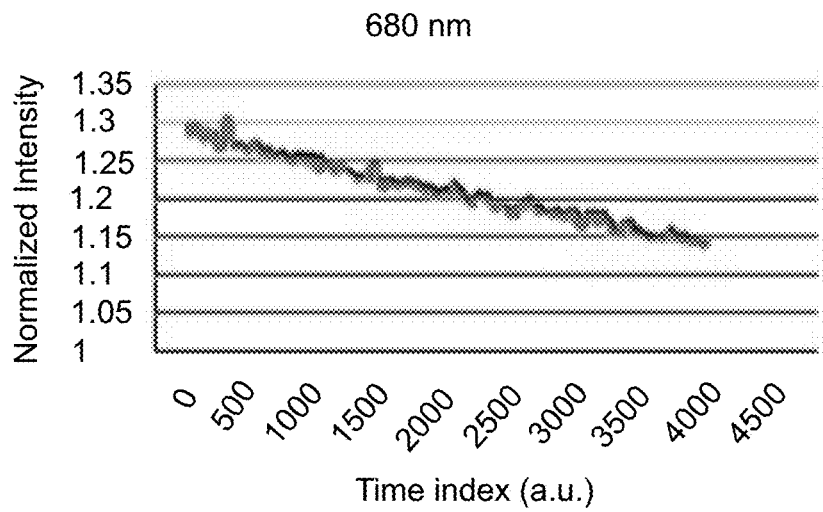
Figure 10E:
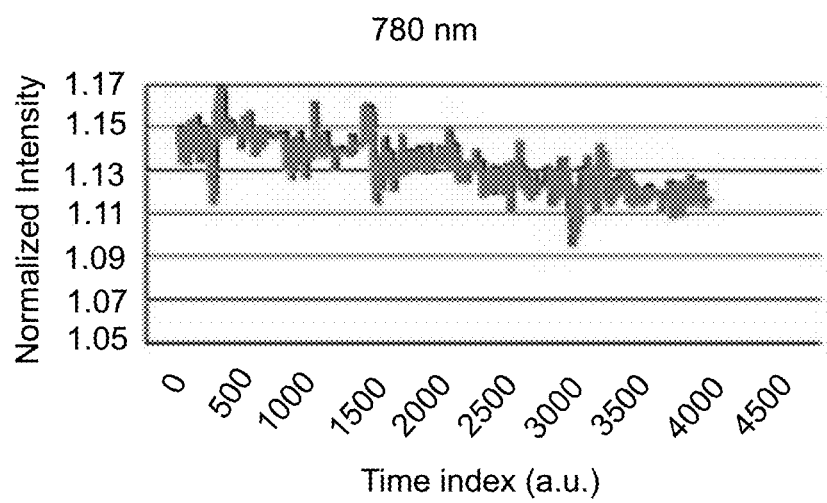
Figure 10F:
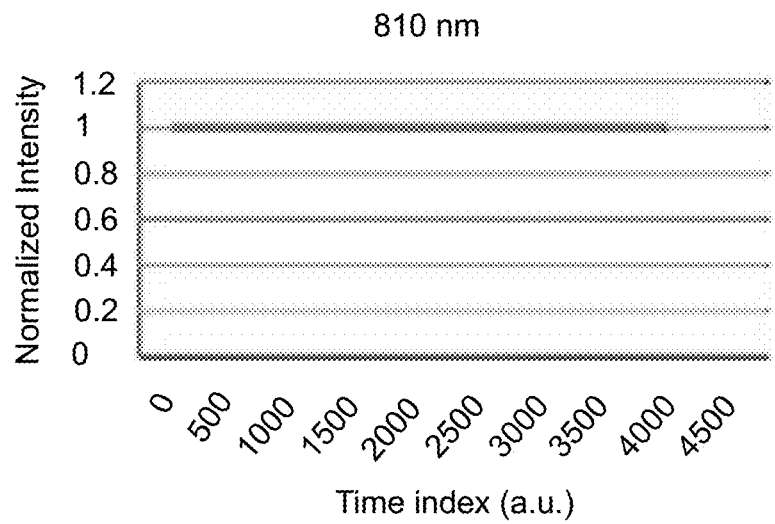
Figure 10G:
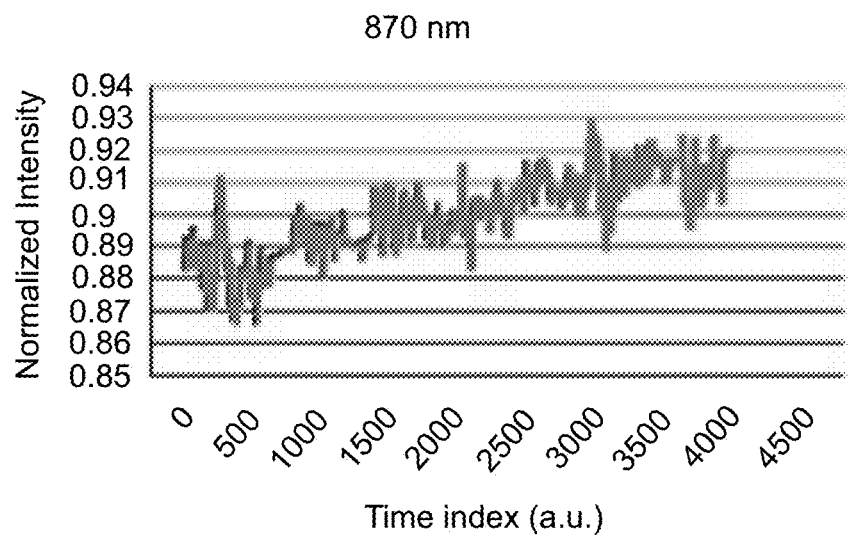
Figure 10H:
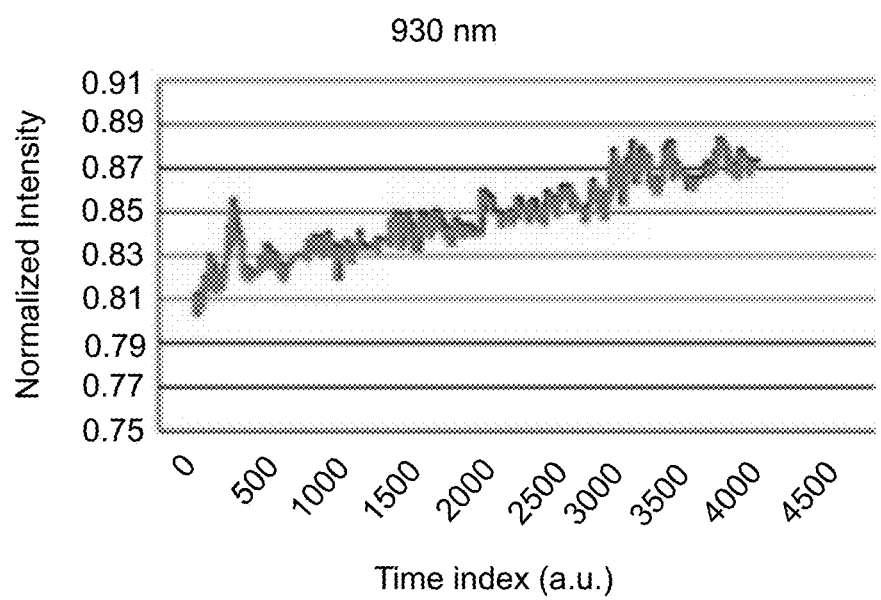

The results of the cuff test are plotted as normalized wavelength intensities and demonstrate that signal intensity decreases for 590 nm, 625 nm, and 680 nm (FIGS. 10B-10D) as oxygen is decreasing and that signal intensity decreases for 870 nm and 930 nm (FIGS. 10G-10H) as oxygen is decreasing. Signal intensity is flat for 780 nm (FIG. 10E) which is near the isosbestic point of ~805 nm and for 525 nm (FIG. 10A) which is a second isosbestic point. FIG. 10F for 810 nm thus shows a normalized wavelength intensity of 1.

Correlation with Predicate Device

Figure 11A:
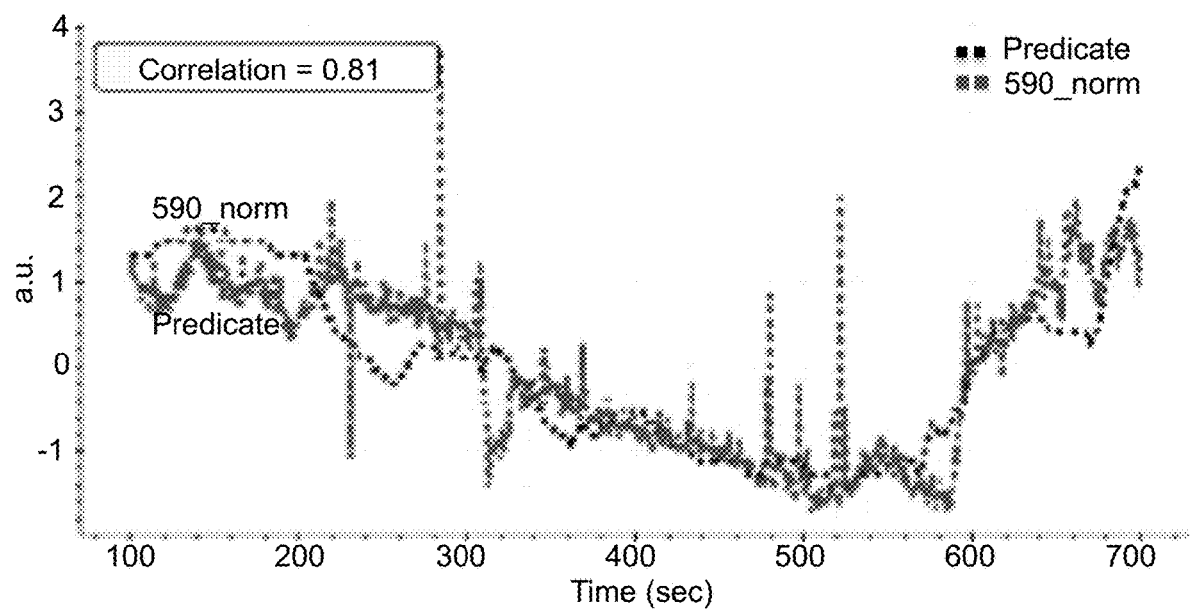
FIGS. 11A-11C show the correlation of oxygen saturation ($StO_2$) measurements obtained at an excitation wavelength of 590 nm with the medical device of FIG. 2 and a predicate device. Measurements are shown before median filtering (FIG. 11A) and after median filtering (FIG. 11B).
Figure 11B:
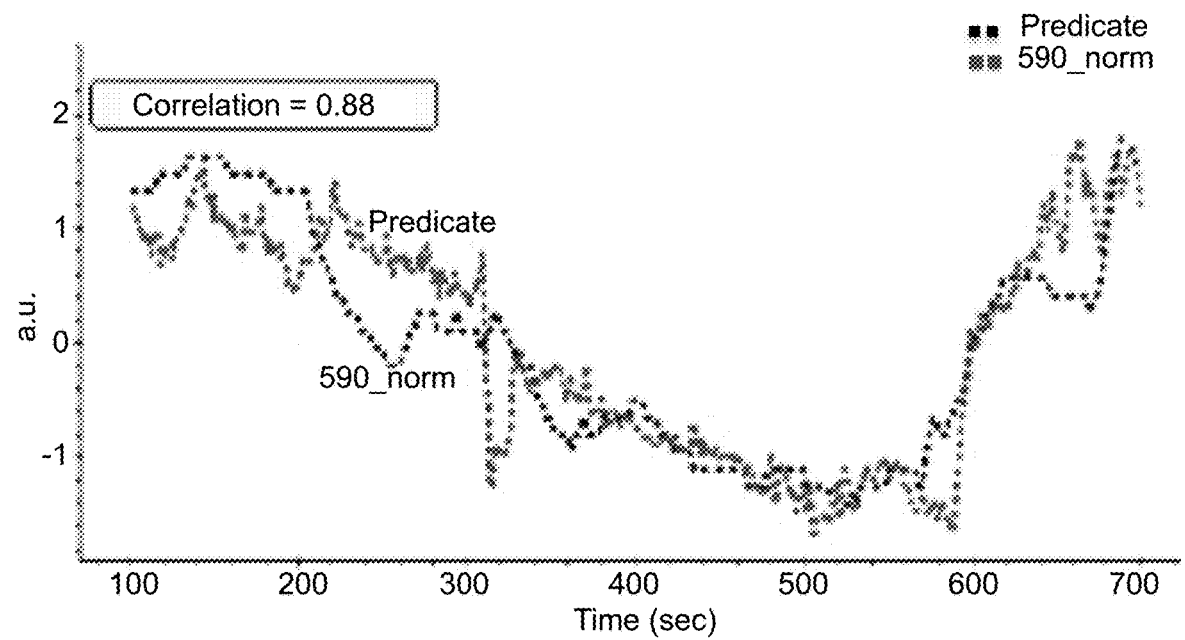

The cuff test was performed while acquiring data from a predicate device (InSpectra StO$_2$, Hutchinson Technology) while simultaneously collecting data as done for the cuff test above (FIGS. 11A-11B). The device was placed across the thenar region of test subject's palm. The InSpectra3 device from Hutchinson Corp. was also placed to capture the gold standard StO$_2$ value. A pressure cuff was attached to the test subject's arm and was set at 160 mmHg, higher than the test subject's systolic pressure. Towards the end of the experiments, the cuff pressure was released to let arterial blood back into the subjects' palm which consequently increases tissue oxygenation levels. The normalized reflected intensities ($N_i = A_i/A_{805\ nm}$, $A_i$=reflected intensity of light at ith wavelength index) of the 8 different wavelengths were then given to a regression model to predict a StO$_2$ value as close as possible to the gold standard StO2 values. Predicted StO$_2$(t)=$\Sigma_{i=1}^{8} r_i N_i(t)$| so that |Predicted StO$_2$(t)−Gold standard StO$_2$(t)| is minimized.

Figure 11C:
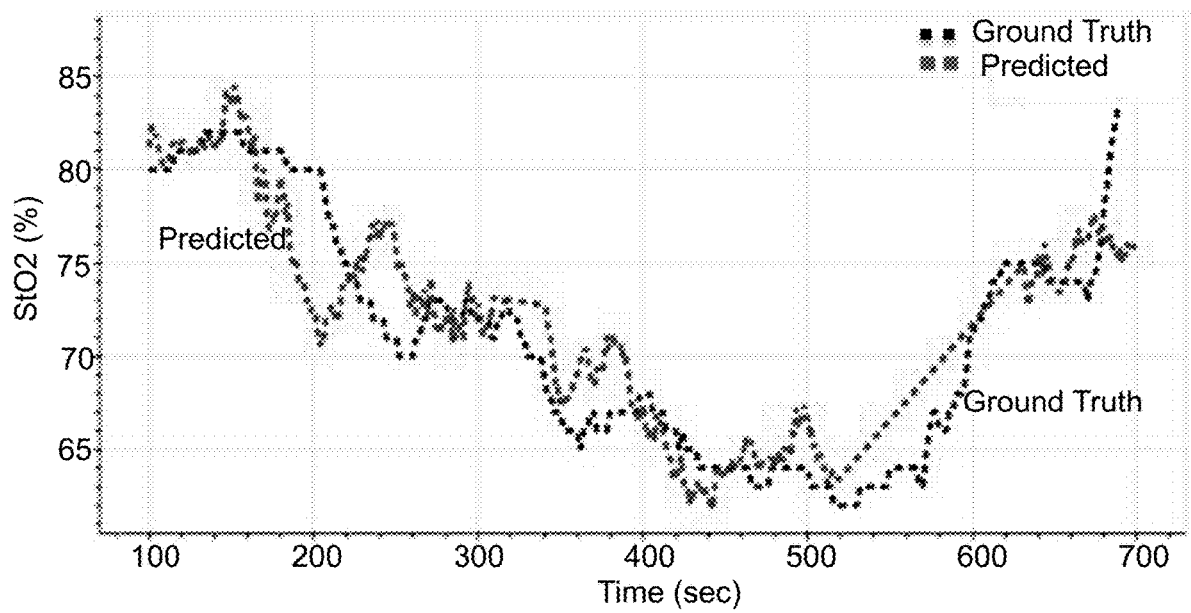

The correlation of the 590 nm wavelength with the predicate device for one wavelength is 0.88 (FIG. 11B). Multiple wavelengths with a greater than 0.70 correlation are used with a multiple regression algorithm to predict oxygen saturation (StO$_2$). FIG. 11C is a plot where the predicted StO$_2$ values and the gold standard, ground truth StO$_2$ values are overlaid. In this prediction a correlation of <90% was observed between the predicted StO$_2$ and the ground truth and the average prediction error was <5%.

Example 2

Figure 12:
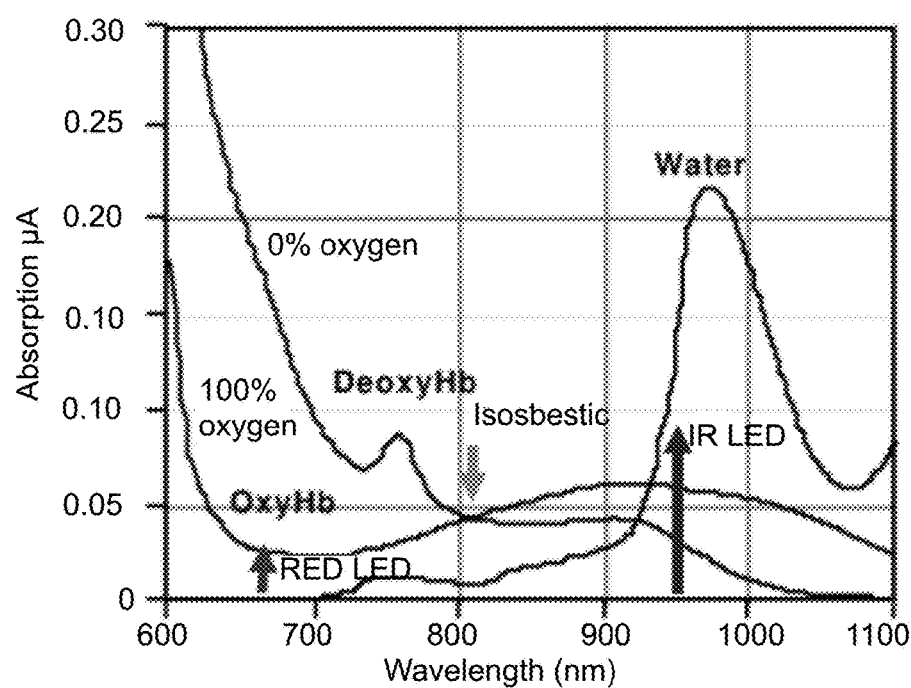
FIG. 12 is an in vitro absorption spectra of hemoglobin and water over a wavelength range of 600 nm to 1100 nm.

Medical Device: Portable Device for Detection of Pressure Ulcers Wavelengths for Pressure Ulcers FIG. 12 is an in vitro absorption spectra of hemoglobin and water showing a spectral window in tissue in the near infrared (NIR) window. The window occurs due firstly a decrease in blood (oxy- and deoxyhemoglobin) absorption and secondly an increase in water absorption with increasing wavelength. With less oxygen in the blood, there is greater red absorption (660 nm) and a lower signal at the photodetector. With more water due to edema, there is greater absorption at 950 nm and a lower intensity at the photodetector.

Classifier Algorithm Fuses Data

The wavelength response is used to classify tissue damage as a pressure ulcer. Raw data is collected from the subject. The wavelength intensity of the light in each pixel of the raw data are fused in a cluster analysis by a classifier algorithm (ncbi.nlm.nih.gov/pmc/articles/PMC4991589). The resulting classified image identifies regions of injury.

Example 3

Medical Device: Wireless Platform for Monitoring Post-Surgical Flap Patch Design The wireless platform, such as BLUETOOTH enabled (Bluetooth SIG), has a control patch, a flap patch and a reusable receiver with a display device. The control patch monitors the healthy tissue temperature, while the flap patch monitors both flap temperature and $StO_2$. FIGS. 6A-6B illustrate the components and electronic communication among them in the wireless platform framework.

The MAXREFDES282 Health Patch Platform (Analog Devices, Inc., Wilmington, MA) is the building block on which the patch is constructed and can measure the peripheral capillary oxygen saturation ($SpO_2$), the surface temperature of the tissue to which it adheres, and the ambient temperature of the environment. The temperature measurements, however, are affected by the proximity of active light-emitting diodes (LEDs) required for $StO_2$ monitoring. To eliminate this error, the patch is re-engineered to extract and separate the LEDs from the temperature sensor, i.e., re-engineering the printed circuit board design of the MAXREFDES282 that is provided with the device. Moreover, an insulating material is placed between the ambient measuring temperature sensor and the tissue surface temperature sensor to minimize any heat flow from the tissue surface to the ambient measuring temperature sensor.

Additionally, the MAXREFDES282 platform only utilizes two LEDs, and, therefore, two wavelengths, i.e., one at red wavelength and an infrared (IR) wavelength, to measure $SpO_2$. Disruption of perfusion to a flap can result in flap necrosis and tissue loss. If blood supply is low, the pulse to the flap may also be minimal. Unlike a $SpO_2$ measurement that requires the ratio of pulse amplitudes of the reflected red and IR light that passes through pulsing tissue, a $StO_2$ measurement can be done without the pulsing amplitude information. Therefore, $StO_2$ is a more suitable solution to continuously monitor the tissue health of surgical flaps and prevent failures.

To make the patch multispectral and to increase accuracy for $StO_2$ monitoring, additional wavelengths are required. In addition to separating the LEDs from the temperature measuring side of the patch, the configuration is designed to include additional LEDs, increasing the number of wavelengths from two to four wavelengths of 625 nm, 680 nm, 805 nm, and 870 nm. Two wavelengths, 625 nm and 680 nm, are below the isosbestic point of 805 nm and one wavelength 870 nm is above the isosbestic point. The isosbestic point is the wavelength where oxygenated and deoxygenated blood absorbs light equally. This ratio of wavelengths to the isosbestic point improves the repeatability and accuracy of the measurement. As oxygen in the blood decreases, the intensities of reflected lights of wavelengths below the isosbestic decreases while those above the isosbestic wavelength increase. The wavelengths below the isosbestic point have higher sensitivity and hence using two wavelengths below the isosbestic point increases measurement accuracy.

In Vitro Testing Using Phantom Tissues

A phantom tissue created with a similar thermal conductivity as the soft tissue of the flap is used for in vitro tests. The thermal conductivity of the tissue is calculated as in Example 1. The thermal conductivity in the phantom tissue is similar to human tissue and calculations can accurately predict how the patches perform on a patient. The phantom tissues are created by adding three layers of low-density polyethylene (LDPE), and Avery MED 3044 double-sided adhesive to stack multiple layers of LDPE together.

Figure 13A:
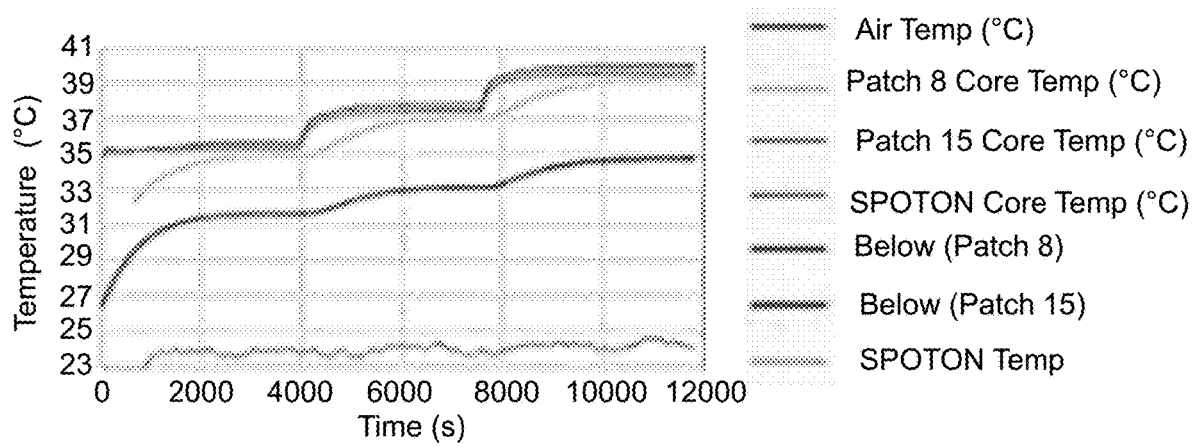
FIGS. 13A-13D compare core temperature measurements taken by the temperature patch comprising the wireless platform and a predicated device, i.e., the SPOTON system from the 3M company on a phantom (FIGS. 13A-13C) and in a healthy human subject (FIG. 13D).
Figure 13B:
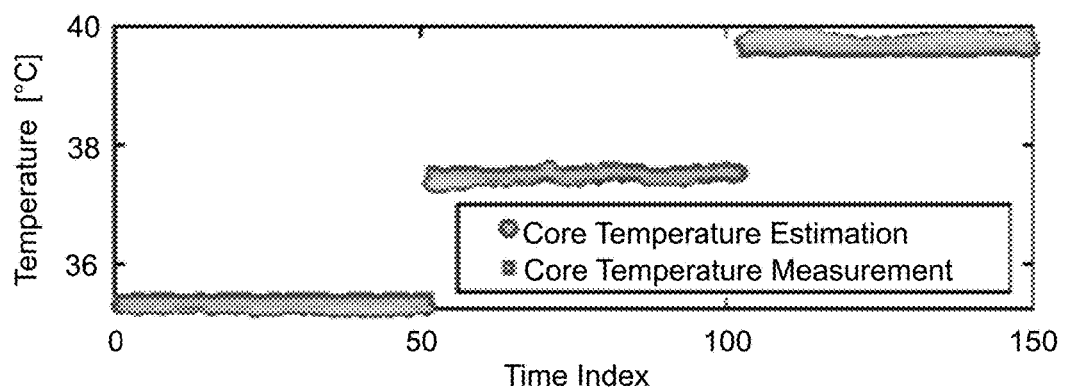
Figure 13C:
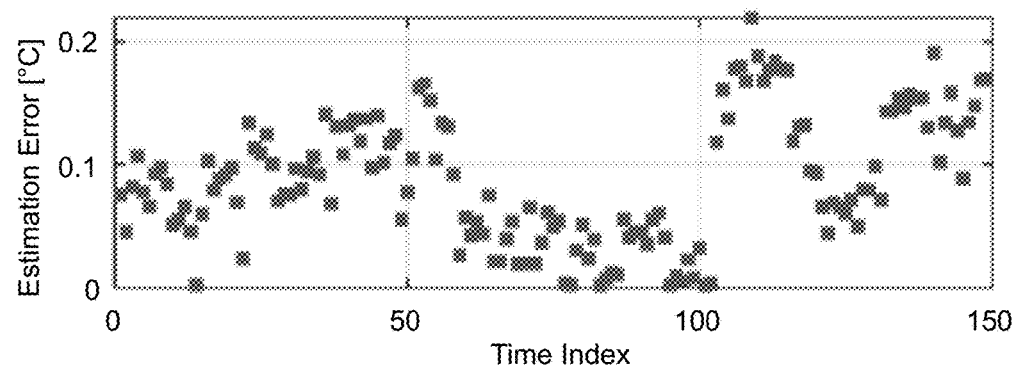
Figure 13D:
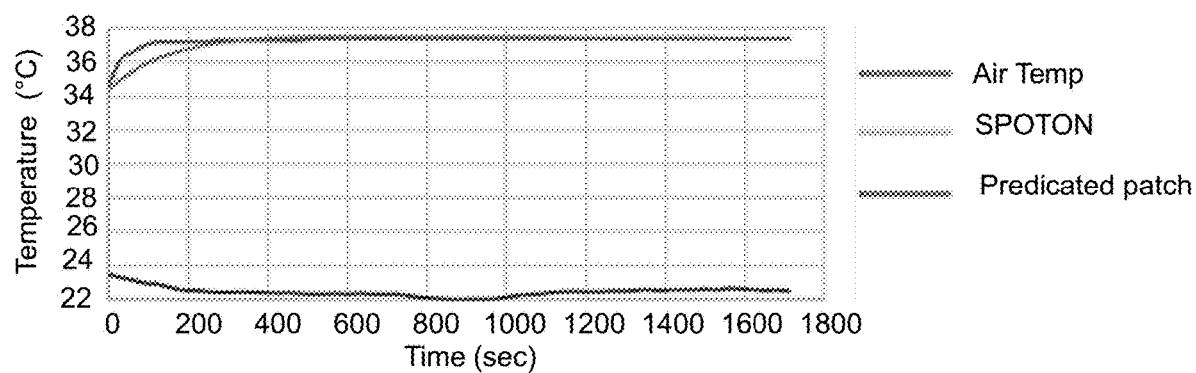

Temperature testing was performed using the phantom and a hot plate. The temperature patch, a SPOTON (3M Company, St. Paul, MN), a non-invasive system that measures the core body temperature of patients, core temperature sensors, and an air temperature sensor were placed on the phantom. Temperature recordings were made with the temperature sensing patch with the max30205 sensor and the SPOTON. Raw data (FIG. 13A) from this set up shows how the temperature sensing patch reacts to changes in core temperature over time in comparison to the SPOTON. The error for the temperature sensing patch at a steady state was <0.2° C. (FIGS. 13B-13C). The test was performed on healthy human subjects using the temperature sensing patch and the SPOTON. The results show that the patch can estimate the core temperature of a human subject comparable to that of the SPOTON (FIG. 13D).

In Vivo Testing of the Patch in Porcine Models

Eight pigs are used for in vivo testing of the patch, where two rectus abdominus myocutaneous flaps are harvested per pig.

Anesthesia: Swine are housed individually in pens, fed ad libetum with standard hog feed, and are fasted for 24 h before the procedure, with free access to water and up to two 500 cc bottles of regular Gatorade™. On day zero, each pig undergoes induction with ketamine (Zoetis, 2.2 mg/kg), Telazol® (Zoetis; 4.4 mg/kg), and xylazine (Zoetis; 2.2 mg/kg), given as a single IM injection. Each pig is weighed and endotracheally intubated. EKG, pulse oximetry, rectal temperature, and lingual end-tidal CO2 monitors are placed. The pig is allowed to rest on a water-circulated warming blanket set at 102° F. An auricular intravenous (IV) line is placed. Anesthesia is maintained with isoflurane (0.5-1%) and supplemental oxygen (3-5 L/min) using a MATRX ventilator (midmark.com). The ventilator rate initially is set at 12-15 breaths per minute with a tidal volume of 10 mL/kg, and subsequently is adjusted to maintain the $EtCO_2$ at 40-50 mm Hg. Cotton blankets are placed over non-surgical areas to minimize any decrease in body temperature. Vital signs are continuously recorded on a laptop computer via a Bionet BM5 monitor.

Rectus myocutaneous flap harvest: Flap harvesting procedures are performed under 4× binocular loupe magnification. A pedicled rectus abdominus myocutaneous flap is raised based on the deep superior epigastric artery and veins in addition to the superficial superior epigastric vein. A plastic surgeon specialized in flap and microsurgery does the procedure. The main pedicle is detected on the skin using an 8-MHz pencil Doppler probe. With the pig under general anesthesia and in the supine position, the chest, abdomen, groins, and bilateral lower extremities are shaved with an electric clipper, washed with soap and water, and then prepped using ChloraPrep™ applicators (chlorhexidine gluconate/isopropyl alcohol). The flap is harvested by creating 2 rectangular flaps designed over the rectus muscle, one flap on each side of the abdomen, and each flap is centered over the underlying rectus muscle. The skin flap is designed with a surgical marker over the rectus muscle. The skin flap always remains attached to the underlying rectus muscle, perforators are not explored or identified, or dissected. The skin superior border begins at the subchondral border, followed by a midline incision down to the umbilicus. The inferior border of the flap is located at the umbilicus level and extends laterally past the lateral border of the rectus muscle. Each flap on both sides of the abdominal midline is the same dimension. The skin paddle of the flap ill represents the surface area and boundaries of the underlying rectus muscle and is shaped as a rectangle (superior border: subchondral region, midline, lateral border of the rectus muscle, lateral border of the rectus muscle. The superior skin incision is made first to identify the location and width of the underlying rectus muscle. The skin incision width is adjusted based on the width of the underlying rectus muscle.

Once the width of the rectus muscle is confirmed, this determines the width of the skin incision in the subchondral region. The vertical flap skin incision is then made just lateral to the edge of the rectus muscle down to the umbilicus level of the abdomen. A transverse skin incision is made at the umbilicus level and equal to the width of the rectus muscle. A central vertical midline incision is made in between both rectus muscles to connect the superior border of the flap with the inferior border of the flap. Once the skin incision is made circumferentially around the flap and once all borders of the rectus have been identified, the superior superficial epigastric vein is identified within the subcutaneous tissue and is found superficial to the rectus muscle. The superior superficial epigastric veins are found more lateral and more superficial than the superior epigastric vein and artery. The rectus muscle is dissected at the superior border of the fap to identify the underlying SEA and SEV (superior epigastric artery and superior epigastric vein). The superior epigastric artery and vein are identified deep in the rectus muscle and are found medial to the superior superficial epigastric vein. Once the superior rectus muscle is dissected, attention is given to the inferior border of the flap where the rectus muscle is dissected and cut in a transverse direction (same procedure as superior rectus dissection). The SEA and SEV and SSEV is always kept intact for each flap. At this point, the rectus muscle flap is completely detached and is separated from the rest of the caudal and cephalad portions of the rectus muscle as well as the anterior sheath of the abdominal wall fascia underneath the rectus, and the midline centrally.

Monitoring $StO_2$ and Temperature Via the Patch

The patch is attached to the central portion of the flap along with the Vioptix probe which serves as a control. Both probes are positioned over the central portion of the flap and are 2-3 cm from each other. Flap perfusion readings are measured at 1-minute intervals for 15 minutes until baseline reading is reached for tissue oxygenation for both the Vioptix probe and for the A BLUETOOTH connection is established with the patch probe. The ViOptix T.Ox probe is connected to the external monitor via the fiber optic cable which is attached to the monitor.

Baseline flap readings: A stable reading is taken after 15 minutes and recorded for both the experimental probe and the Vioptix probe. Three readings are taken at 5-minute intervals after an initial baseline of 15 min.

Venous congestion experiment: An Acland clamp is applied to the superior epigastric vein and the superior superficial epigastric vein for 15 min. After 15 min the readings on the experimental probe and Vioptix probe are taken, and three readings are taken at 5-minute intervals. After the last reading, the Acland clamp is removed and the flap is left to re-stabilize for 15 min before starting the arterial ischemia experiment.

Arterial ischemia experiment: An Acland clamp is applied to the deep superior epigastric artery for 15 min. Tissue Oxygenation measurements are taken after 15 min baseline with the Vioptix probe and experimental probe. Readings are taken every 5 minutes after the 15 min baseline. Three recordings are taken in total every 5 minutes for both probes. The entire procedure (baseline readings, Venous congestion experiment and readings, arterial ischemia experiment, and readings) are repeated three times for each flap. After completion of all experiments, the flap skin is closed to the peripheral wound using resorbable Vicryl sutures and skin staples, and the Vioptix probe is removed. A surgical dressing is placed on the surgical wound. The experimental probe is kept in place and secured for 5 days. The experimental probe is securely covered to avoid trauma and contact loss from the underlying skin flap. Measurements are taken every 5 minutes for $StO_2$. Oxygen saturation is measured as in Example 1.

What is claimed:

1. A medical device for measuring tissue properties in a subject, comprising:
   a light-guiding cone comprising an opaque, anti-reflective, sloped surface and having optical properties that direct light along an optical excitation path into a homogeneous field on a tissue of interest in the subject;
   a plurality of excitation light sources disposed at an open end of the light-guiding cone, each of said plurality emitting light at a wavelength from visible to near infrared;
   an image sensor configured to measure intensities of light with different wavelengths reflected from the tissue of interest;
   a radially extruded lip at the end of the light-guiding cone disposed to cover an area of the tissue of interest under interrogation and to prevent ambient light from impinging on the area;
   at least one pressure sensor configured to sense conformal attachment of the medical device to the surface of the tissue of interest;
   and
   a processor and a memory in electronic communication with the device and tangibly storing an algorithm for processing the reflected wavelengths as a measurement of tissue properties, said algorithm comprising processor-executable instructions that perform all of the following to:
   predict an Ankle Brachial Index from measurements of tissue oxygenation, tissue temperature, or perfusion index or a combination thereof at at least one wavelength;
   correlate tissue oxygenation measurements from an upper limb and a lower limb of the subject to the Ankle Brachial Index;
   measure a photoplethysmography signal; and
   predict peripheral artery disease in the subject.

2. The medical device of claim 1, further comprising:
   a removable optically clear cap comprising a sterile barrier and disposed between the device and the tissue of interest;
   an optical diffuser positioned on the optical excitation path configured to direct the light into the homogeneous field on the tissue of interest;
   a temperature sensor to measure a surface temperature of the tissue of interest,
   at least one accelerometer to remove effects of tissue or device movement during data calibration or during data acquisition; or
   a display to monitor tissue properties; or
   a combination thereof.

3. The medical device of claim 1, wherein the light-guiding cone further comprises an impedance sensor for detecting moisture content in the tissue.

4. The medical device of claim 1, wherein the light-guiding cone comprises at least one reflective material and is configured for automatic self-calibration.

5. The medical device of claim 1, wherein the image sensor comprises a photodiode or an array of photodiodes.

6. The medical device of claim 1, further comprising a printed circuit board in operable communication with the device, said printed circuit board comprising at least one accelerometer therewithin to quantify movements of the device.

7. The medical device of claim 1, wherein one of the wavelengths emitted from the plurality of excitation light sources is an isosbestic point, that ranges from 800 nm to 805 nm, in a ratiometric image sensor measurement of a non-isosbestic wavelength to the isosbestic wavelength.

8. The medical device of claim 1, wherein the algorithm further comprises processor-executable instructions configured to:
    calculate distance from the image sensor to the tissue of interest via an analysis of patterns of light formed on the surface of the tissue of interest;
    predict the stage of at least one pressure ulcer in the subject as stage 1, stage 2, stage 3, or stage 4; or
    predict sub-clinical stage 1 pressure ulcers in the subject; or
    a combination thereof.

9. A method for measuring tissue properties in a subject, comprising the steps of:
    a) illuminating a tissue of interest in the subject with a non-isosbestic wavelength emitted from the plurality of excitation light sources comprising the medical device of claim 1;
    b) measuring a reflected non-isosbestic wavelength via the image sensor comprising the device;
    c) illuminating the tissue of interest with an isosbestic wavelength;
    d) measuring a reflected isosbestic wavelength;
    e) determining a ratiometric image sensor measurement of the reflected non-isosbestic wavelength to the reflected isosbestic wavelength via the algorithm comprising the medical device;
    f) correlating the ratiometric image sensor measurement with at least one tissue property of the tissue of interest; and
    g) repeating steps a) to f) at least once with another non-isosbestic wavelength and the isobestic wavelength.

10. The method of claim 9, further comprising:
    measuring the tissue properties to determine a baseline;
    measuring the tissue properties as the subject exercises;
    measuring the tissue properties during a recovery period after exercise is completed;
    measuring a recovery time of the tissue properties; and
    correlating, via the algorithm, the recovery time with an ankle brachial index in the subject or to predict severity of peripheral arterial disease in the subject.

11. The method of claim 9, wherein steps a) to d) comprise:
    illuminating sequentially the tissue of interest with a plurality of non-isosbestic wavelengths of differing wavelengths; and
    measuring sequentially the plurality of reflected isosbestic wavelengths;
    illuminating sequentially the tissue of interest with a plurality of isosbestic wavelengths of differing wavelengths; and
    measuring sequentially the plurality of reflected isosbestic wavelengths.

* * * * *